United States Patent
Emerick et al.

(10) Patent No.: US 9,693,877 B2
(45) Date of Patent: Jul. 4, 2017

(54) EXPANDABLE TISSUE SPACE IMPLANT AND METHOD OF USE

(71) Applicant: MEDIVEST, LLC, Columbia City, IN (US)

(72) Inventors: Brian G. Emerick, Columbia City, IN (US); Jeffrey A. Farris, Berne, IN (US); Brent Walter, Huntington, IN (US); Heidi Stamets, Monroeville, IN (US)

(*) Notice: Subject to any disclaimer, the term of this patent is extended or adjusted under 35 U.S.C. 154(b) by 68 days.

(21) Appl. No.: 14/406,013

(22) PCT Filed: Jun. 6, 2013

(86) PCT No.: PCT/US2013/044563
§ 371 (c)(1),
(2) Date: Dec. 5, 2014

(87) PCT Pub. No.: WO2013/184946
PCT Pub. Date: Dec. 12, 2013

(65) Prior Publication Data
US 2015/0182346 A1    Jul. 2, 2015

Related U.S. Application Data

(60) Provisional application No. 61/656,283, filed on Jun. 6, 2012.

(51) Int. Cl.
*A61F 2/44* (2006.01)
*A61F 2/46* (2006.01)
(Continued)

(52) U.S. Cl.
CPC ............ *A61F 2/447* (2013.01); *A61F 2/4465* (2013.01); *A61F 2/4611* (2013.01);
(Continued)

(58) Field of Classification Search
CPC .............................................. A61F 2/44–2/447
(Continued)

(56) References Cited

U.S. PATENT DOCUMENTS 6,616,695 B1 * 9/2003 Crozet ................ A61F 2/30744
606/246
7,214,243 B2   5/2007 Taylor
(Continued)

FOREIGN PATENT DOCUMENTS

WO       2005006944 A2    1/2005
WO    WO 2011060071 A1 *  5/2011 ............... A61F 2/44

OTHER PUBLICATIONS

International Search Report for PCT/US2013/044563 dated Sep. 6, 2013.

*Primary Examiner* — Nicholas Plionis
(74) *Attorney, Agent, or Firm* — Heslin Rothenberg Farley & Mesiti P.C.; John Boger

(57) ABSTRACT

A horizontal and vertical expandable tissue spacer implants, insertion tools, assembly methods and surgical methods are disclosed. The horizontal expandable tissue spacer implant includes a first lateral member with a first side, a second lateral member with a first side, and an intermediate spacer member. The intermediate spacer member is adapted to cooperatively engage and hold the first side of the first lateral member and the first side of the second lateral member. A vertical expandable tissue spacer implant includes a top member with a bottom surface, a bottom member with a top surface, and an intermediate spacer member with a coupling mechanism. The coupling mechanism cooperatively engages the bottom surface of the top member to the intermediate spacer member and the top surface of the bottom member to the intermediate spacer member.

18 Claims, 26 Drawing Sheets

(51) Int. Cl.
    *A61F 2/28*     (2006.01)
    *A61F 2/30*     (2006.01)
(52) U.S. Cl.
    CPC .......... *A61F 2/4684* (2013.01); *A61F 2/3094* (2013.01); *A61F 2002/2835* (2013.01); *A61F 2002/305* (2013.01); *A61F 2002/30013* (2013.01); *A61F 2002/3084* (2013.01); *A61F 2002/30387* (2013.01); *A61F 2002/30388* (2013.01); *A61F 2002/30398* (2013.01); *A61F 2002/30481* (2013.01); *A61F 2002/30502* (2013.01); *A61F 2002/30504* (2013.01); *A61F 2002/30505* (2013.01); *A61F 2002/30509* (2013.01); *A61F 2002/30579* (2013.01); *A61F 2002/30607* (2013.01); *A61F 2002/30616* (2013.01); *A61F 2002/30828* (2013.01); *A61F 2002/30892* (2013.01); *A61F 2002/4475* (2013.01); *A61F 2002/4628* (2013.01); *A61F 2002/4629* (2013.01); *A61F 2002/4661* (2013.01); *A61F 2310/00011* (2013.01); *A61F 2310/00017* (2013.01); *A61F 2310/00023* (2013.01); *Y10T 29/49947* (2015.01)

(58) Field of Classification Search
    USPC .......................................... 623/17.11–17.16
    See application file for complete search history.

(56) References Cited

U.S. PATENT DOCUMENTS

| | | | |
|---|---|---|---|
| 2002/0099444 A1* | 7/2002 | Boyd | A61F 2/28 623/17.16 |
| 2007/0225726 A1* | 9/2007 | Dye | A61F 2/4465 606/99 |
| 2008/0021559 A1* | 1/2008 | Thramann | A61F 2/447 623/17.16 |
| 2008/0114357 A1 | 5/2008 | Allard et al. | |
| 2009/0105825 A1 | 4/2009 | Foreman et al. | |
| 2009/0222100 A1* | 9/2009 | Cipoletti | A61F 2/447 623/17.16 |
| 2010/0145394 A1* | 6/2010 | Harvey | A61B 17/7049 606/302 |
| 2010/0179658 A1* | 7/2010 | Freeman | A61F 2/44 623/17.12 |
| 2011/0245927 A1 | 10/2011 | Farris | |

* cited by examiner

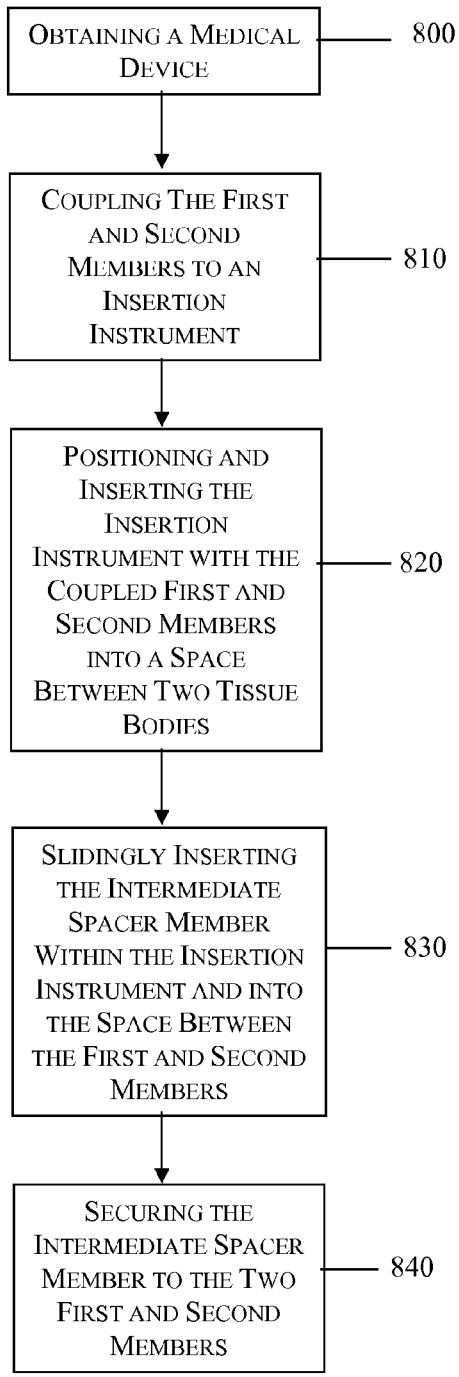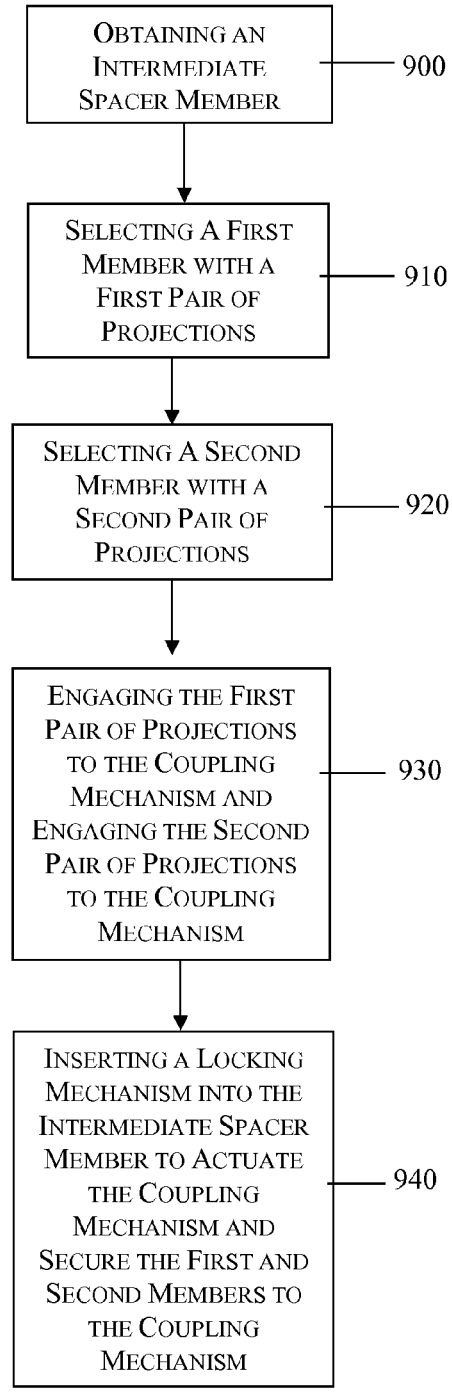
FIG. 60
FIG. 61

EXPANDABLE TISSUE SPACE IMPLANT AND METHOD OF USE

CROSS-REFERENCE TO RELATED APPLICATION

This application is a National Stage application based on International Application PCT/US2013/044563 filed on Jun. 6, 2013, published as WO 2013/184649 on Dec. 12, 2013. This application also claims priority benefit under 35 U.S.C. §119(e) of U.S. provisional application No. 61/656,283 filed Jun. 6, 2012, of which both applications are incorporated herein by reference in their entirety.

TECHNICAL FIELD

The present invention relates generally to general surgery, orthopaedic and neurosurgical implants used for insertion within a space between hard and soft tissue structures, and more specifically, but not exclusively, concerns devices implanted within a bone to replace a resected, fractured or diseased portion and to maintain or reestablish proper spacing between the bone fragments.

BACKGROUND OF THE INVENTION

Damage or disease that affects the integral structure of a bone or other structures, may lead to neurologic impairment or loss of structural support integrity with possible permanent damage to the surrounding soft tissue and adjacent neurologic, vascular and systemic structures. Maintaining or reestablishing anatomic spacing within a bone structure or other structural tissue is critical to ensuring continued functionality and mobility of the patient and avoidance of long-term serious neurological, vascular or other systemic impairments. Please note that the terms "implant" and "device" may be used interchangeably and have the same meaning herein.

SUMMARY OF THE INVENTION

The present invention provides in one aspect, a horizontal expandable tissue spacer implant that includes a first lateral member with a first side, a second lateral member with a first side, and an intermediate spacer member. The intermediate spacer member is adapted to cooperatively engage and hold the first side of the first lateral member and the first side of the second lateral member.

The present invention provides in another aspect, a vertical expandable tissue spacer implant that includes a top member with a bottom surface, a bottom member with a top surface, and an intermediate spacer member with a coupling mechanism. The coupling mechanism cooperatively engages the bottom surface of the top member to the intermediate spacer member and the top surface of the bottom member to the intermediate spacer member.

The present invention provides in a further aspect, a method of assembling an implant, including obtaining an intermediate spacer member having a coupling mechanism, selecting a first member with a first pair of projections and selecting a second member with a second pair of projections. The method may also include engaging the first pair of projections of the first member to the coupling mechanism of the intermediate spacer member and engaging the second pair of projections of the second member to the coupling mechanism of the intermediate spacer member and inserting a locking mechanism into the intermediate spacer member to actuate the coupling mechanism and secure the first member and second member to the intermediate spacer member.

The present invention provides in yet another aspect, a surgical method for maintaining a space between two tissue bodies in a living being, including obtaining a medical device with a first member, a second member, and an intermediate spacer member. The intermediate spacer member includes a coupling mechanism which slidingly couples the first member to the intermediate spacer member and the second member to the intermediate spacer member. The method may also include coupling the first and second members to a distraction or insertion instrument and positioning and inserting the distraction instrument with the coupled first and second members into a space between the two tissue bodies to maintain or increase the space therebetween. Further, the method may also include slidingly inserting the intermediate spacer member within the insertion instrument and into the space between the first and second members and securing the intermediate spacer member to the two first and second members.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features and advantages of the invention are apparent from the following detailed description taken in conjunction with the accompanying drawings in which:

FIG. 60 is a flow chart of the surgical method for inserting an expandable tissue spacer, in accordance with an aspect of the present invention; and FIG. 61 is a flow chart of the method of assembly an expandable tissue spacer, in accordance with an aspect of the present invention.

DETAILED DESCRIPTION OF THE INVENTION

Disclosed herein are several embodiments of a tissue spacer implant and corresponding insertion and measurement instrumentation. Also disclosed herein are surgical implantation methods for implanting the tissue spacer implants using the insertion and measurement instrumentation.

In this detailed description and the following claims, the words proximal, distal, anterior, posterior, medial, lateral, superior and inferior are defined by their standard usage for indicating a particular part of a bone, prosthesis or surgical instrument according to the relative disposition of the surgical instrument or directional terms of reference. For example, "proximal" means the portion of an instrument positioned nearest the torso, while "distal" indicates the part of the instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Also, the terms "implant" and "device" may be used interchangeably and have the same meaning herein.

Figure 1:
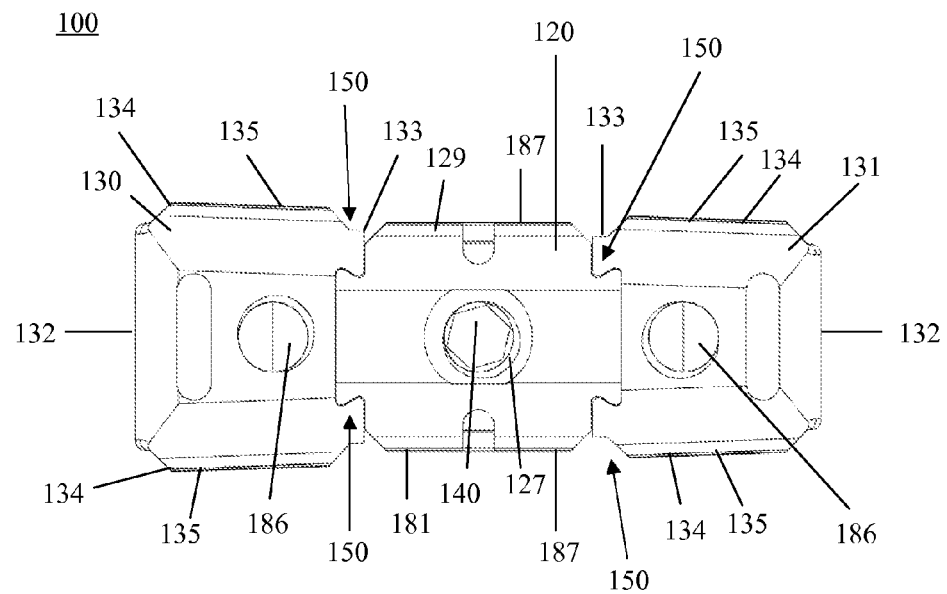
FIG. 1 is a front, elevational view of one embodiment of a horizontal expandable tissue spacer device, in accordance with an aspect of the present invention.
Figure 2:
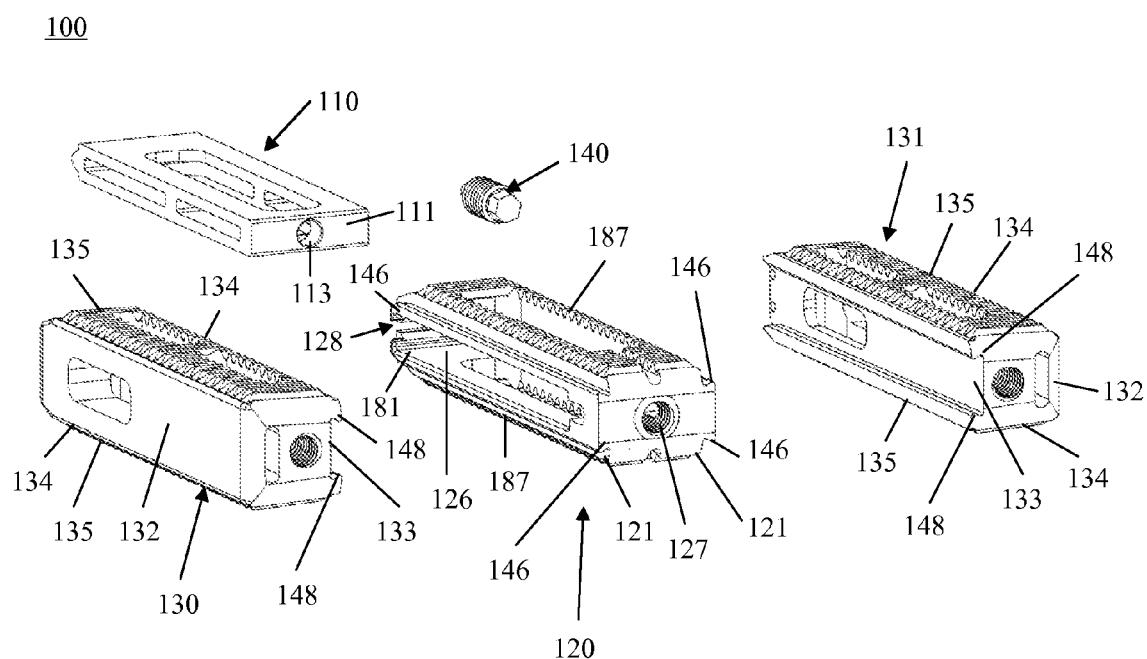
FIG. 2 is an exploded front, elevational view of the tissue spacer device of FIG. 1, in accordance with an aspect of the present invention.

FIG. 1 is a front perspective view of a horizontal tissue spacer implant 100 according to one aspect of the invention. As shown in FIG. 2, the tissue spacer 100 includes a first lateral member 130 and a mirror image, second lateral member 131. Each lateral member 130, 131 includes an outer (lateral directed) side 132 and an inner (medial directed) side 133. The outer side 132 being opposite the inner side 133. The lateral members 130, 131 also include top and bottom sides 134 with bone contacting surfaces 135 disposed one each of the top and bottom sides 134. Each bone contacting surface 135 being configured to engage tissue, for example, bone, such as, vertebrae.

According to aspects of the invention, implant 100 also includes an intermediate spacer member 120 positioned between the first lateral member 130 and the second lateral member 131. The intermediate spacer member 120 includes a first lateral side 121 and a second lateral side 122 opposite the first lateral side 121. The intermediate spacer member 120 typically includes at least two dovetails 146 adapted to couple the inner sides 133 of the two lateral members 130, 131 with the first and second lateral sides 121, 122 of the intermediate spacer member 120. The terms "dovetails," "projections" and "extensions" may be used herein interchangeably as they essentially describe the same component. The two lateral members 130, 131 may be modular and allow the surgeon to mix and match various shaped and configured lateral members 130, 131 with the intermediate spacer member 120.

FIG. 1 also shows the implant construct to have angled top and bottom surfaces when the intermediate spacer 120 is coupled to the two lateral members 130, 131. As seen in FIG. 1 for this example of the implant 100, the left side lateral member 130 has a greater height than the intermediate spacer member 120 and the bone surfaces 135 of the lateral member 130 are angled towards the intermediate spacer member 120. The intermediate spacer member 120 has parallel top and bottom surfaces 129, 181. The intermediate spacer member 130 is coupled to the right side lateral member 131. The lateral member 131 has bone contacting surfaces 135 which are angled away from the intermediate spacer member 120. The lateral side 131 has an overall height that is less than the opposing lateral member 130 to create overall implant angled bone contacting surfaces (top and bottom) that may be used to correct deformities in vivo.

FIG. 2 also shows the other elements that comprise the horizontal tissue spacer implant 100. These include a spacer insert 110 that is positioned within an inner cavity 126 of the intermediate spacer member 120. Coupled to the intermediate spacer member 120 and the spacer insert 110 is a threaded rod or screw 140. The threaded rod 140 is threaded through a first threaded hole 127 in the intermediate spacer member 120 and then projects into the second hole 113 that passes through the front wall 111 of the spacer insert 110. As will become clear when discussing the aspects of the invention, in one aspect, the lateral members 130, 131 may be positioned within a space between two tissue parts (not shown), for example, bone, whereby the intermediate spacer member 120 may be inserted between the lateral members 130, 131. During or after insertion of the intermediate spacer member 120 between the lateral members 130, 131, the coupling mechanism 150 is actuated to attach the three components: the first lateral member 130, the intermediate spacer member 120, and the second lateral member 131. According to aspects of the invention, the coupled members 120, 130, and 131 provide a substantially rigid implant between adjacent tissues, for example, vertebrae. In one aspect of the invention, intermediate spacer member 120 may be provided in a kit that includes a plurality of widths or heights and thicknesses, whereby the intermediate spacer member 120 may be selected from one of these various sizes of intermediate spacer members 120 depending upon the spacing needed between the lateral members 130, 131.

Figure 3:
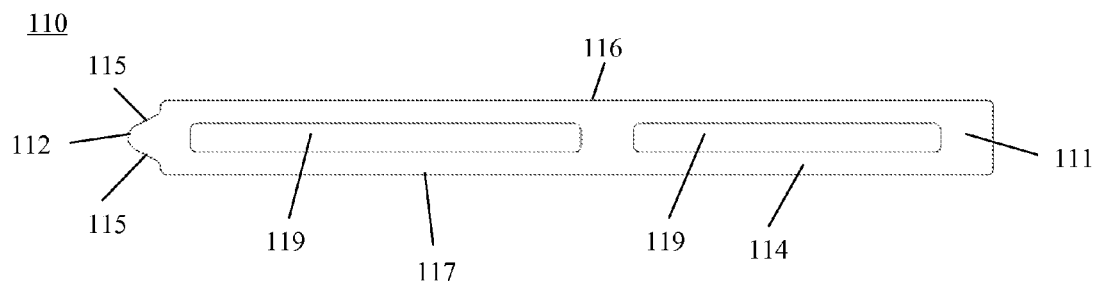
FIG. 3 is a side, elevational view of the insert for the tissue spacer device of FIG. 1, in accordance with an aspect of the present invention.
Figure 4:
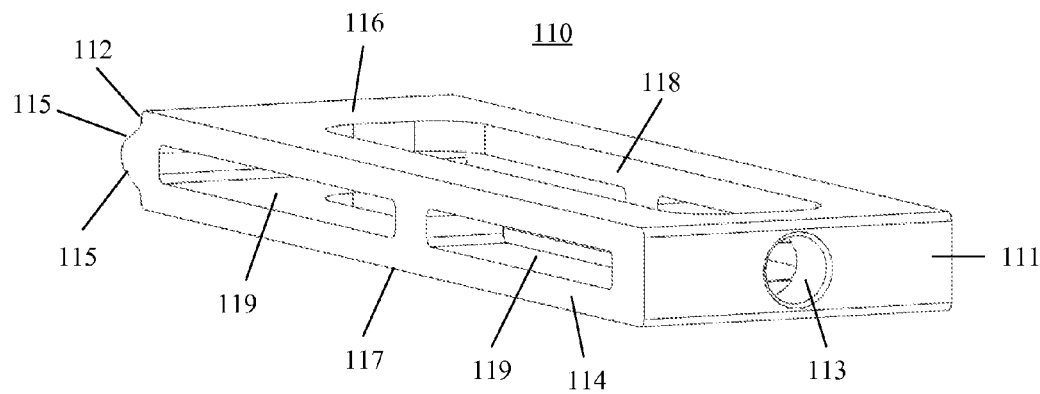
FIG. 4 is a front, perspective view of the insert for the tissue spacer device of FIG. 1, in accordance with an aspect of the present invention.

Referring now to FIGS. 3 and 4, with continued reference to FIGS. 1-2, the spacer insert 110 is shown with a planar front wall 111 and the bullet nose end 112 that is comprised of two angle segments 115. A through hole 113 is seen in the middle portion of the front wall 111. The hole 113 is sized to receive the tip or extension of the threaded rod 140. The spacer insert 110 also includes an opening 118 that passes through the center of the spacer insert 110. The opening 118 is sized to allow the surgeon to pack bone grafting material into and through the entire implant 100. Side through openings 119 are also seen within the lateral sides 114, for facilitating bone graft placement. As seen in FIGS. 3-7, the top and bottom surfaces 116, 117 of the spacer insert 110 are substantially parallel to each other and establish a thickness that supports the top wall 129 and bottom wall 181 of the intermediate spacer member 120 when the spacer insert 110 is within the cavity 126.

Figure 5:
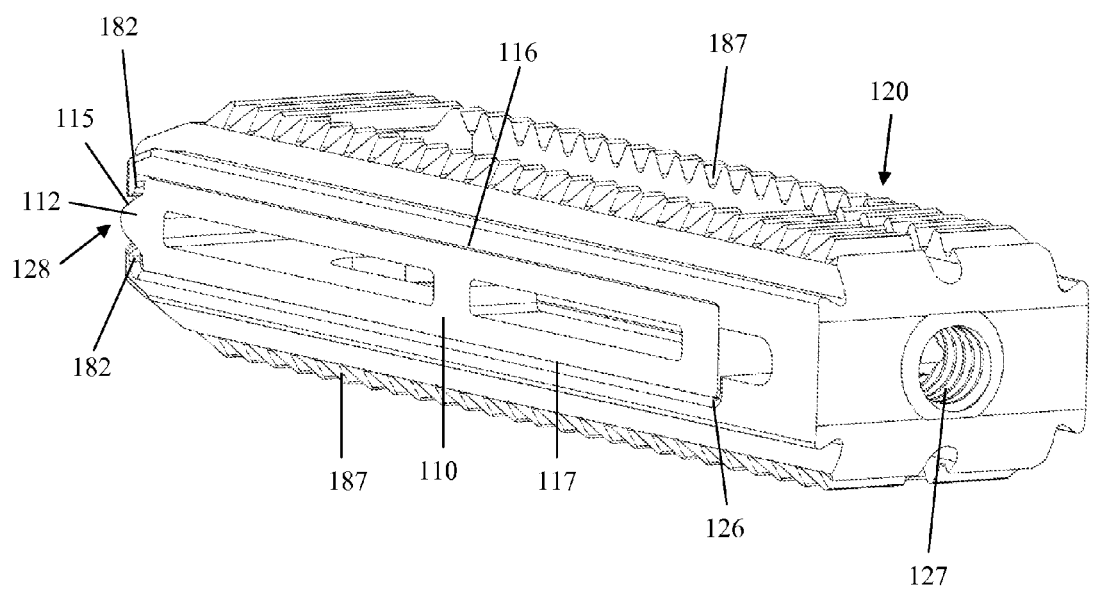
FIG. 5 is a front, perspective view of an intermediate spacer member with the insert in position for the tissue spacer device of FIG. 1, in accordance with an aspect of the present invention.

As seen in FIG. 5, the spacer insert 110 is in place in the inner cavity 126 of the intermediate spacer member 120. The top and bottom surfaces 116, 117 of the spacer insert 110 are adjacent to the top and bottom surfaces of the cavity 126. The front hole 113 of the insert 110 is also aligned with the threaded hole 127 of the intermediate spacer member 120. Further, the angled segments 115 of the bullet nose end 112 are positioned to contact the corresponding angled portions 182 of the rear tapered opening 128 of the intermediate spacer member 120. The relationship of the angled segments 115 of the spacer insert 110 and the angled portions 182 of the intermediate spacer member 120 will function to actuate the coupling mechanism 150 (see FIG. 1) when the threaded rod 140 is rotated within the front hole 127.

Figure 6:
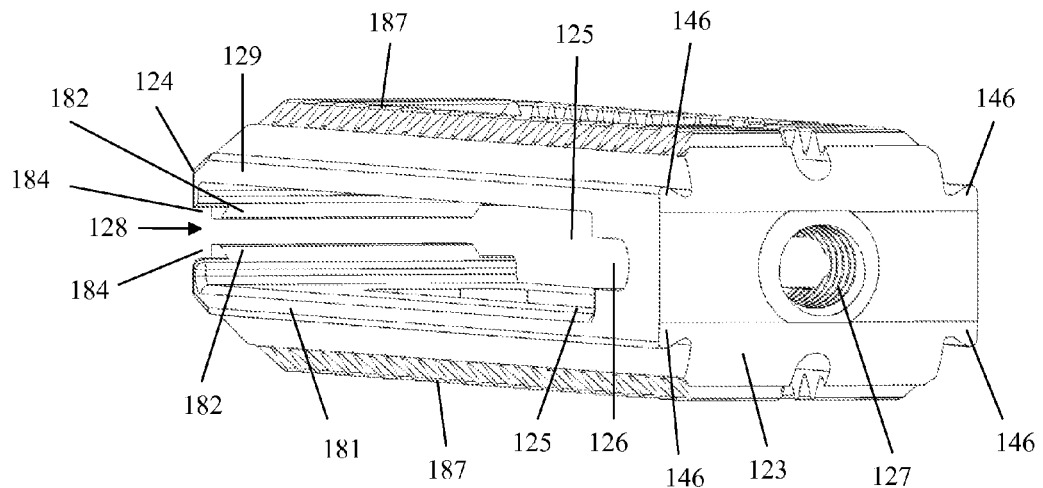
FIG. 6 is a front, perspective view of an intermediate spacer member without the insert in position for the tissue spacer device of FIG. 1, in accordance with an aspect of the present invention.
Figure 7:
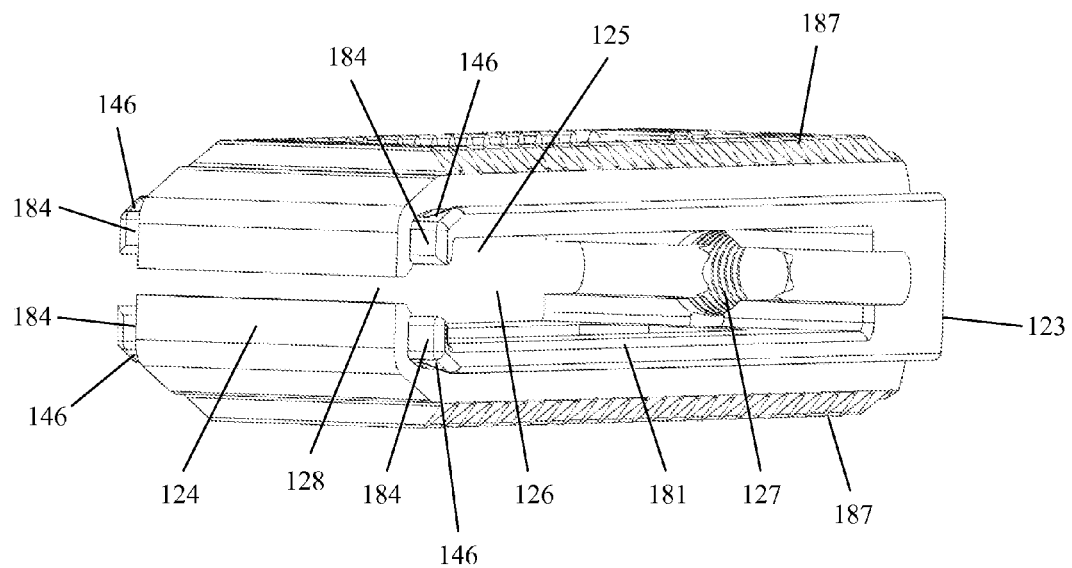
FIG. 7 is a rear, perspective view of the intermediate spacer member without the insert in position for the tissue spacer device of FIG. 1, in accordance with an aspect of the present invention.
Figure 8:
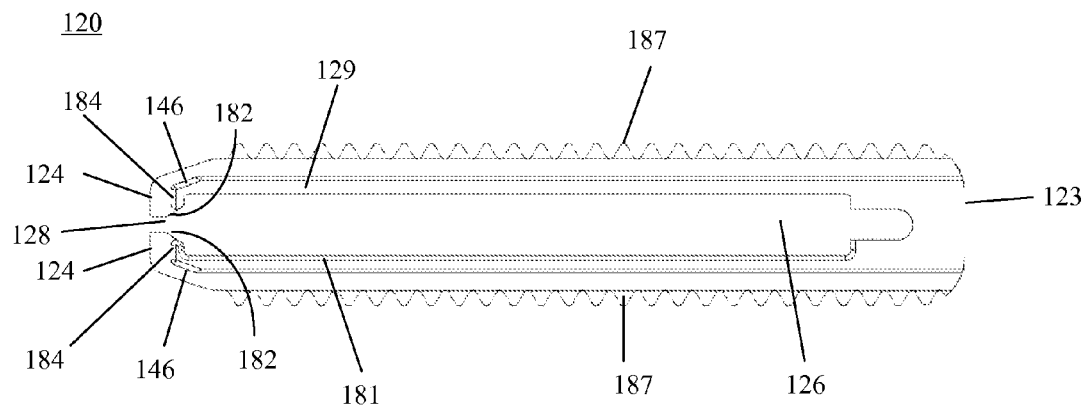
FIG. 8 is a side, elevational view of the intermediate spacer member without the insert in position for the tissue spacer device of FIG. 1, in accordance with an aspect of the present invention.

FIGS. 6 and 7 show the intermediate spacer member 120 without the spacer insert 110 within the cavity 126. As seen in both figures the cavity 126 has a threaded hole 127 at one end and a tapered opening or slot 128 at the opposing end. The cavity 126 also has two opposing side slots 125 through which the spacer insert 110 is inserted. The top and bottom walls 129, 181 are generally parallel (see FIG. 8), but may be angled in an anterior to posterior or medial to lateral directions, depending on the orientation of the implant 100 in the body. Also seen in FIGS. 6 and 7 are longitudinal male dovetails 146 of the coupling mechanism 150 which are positioned on the outer sides of the intermediate spacer member 120. The coupling mechanism 150 also includes female dovetails 148 of the lateral members 130, 131, the spacer insert 110 and the threaded rod 140. Each pair of dovetails 146 has a top element and a bottom element that is generally parallel to each other when the spacer insert 110 is in a first position. When the spacer insert 110 is moved to a second position, wherein the bullet nose 112 makes contact with the angled portions 182 and moves in a rearward direction (towards rear side 124) causing the gap between the angled portions 182 of the rear tapered opening 128 to widen, the top and bottom elements of the dovetails 146 move from a parallel position to an angled or sloped position resulting in the pressing contact with the lateral member female dovetails 148 and the securement of the lateral member 130 to the intermediate spacer member 120. Positioned at the rear side of the dovetails is a stop or notch 184 that is sized to receive a corresponding post (not shown) which may be inserted into openings 136 of the lateral members 130, 131. The stop 184 facilitates holding the lateral members 130, 131 in a constant position relative to the dovetails 146, 148.

Figure 9:
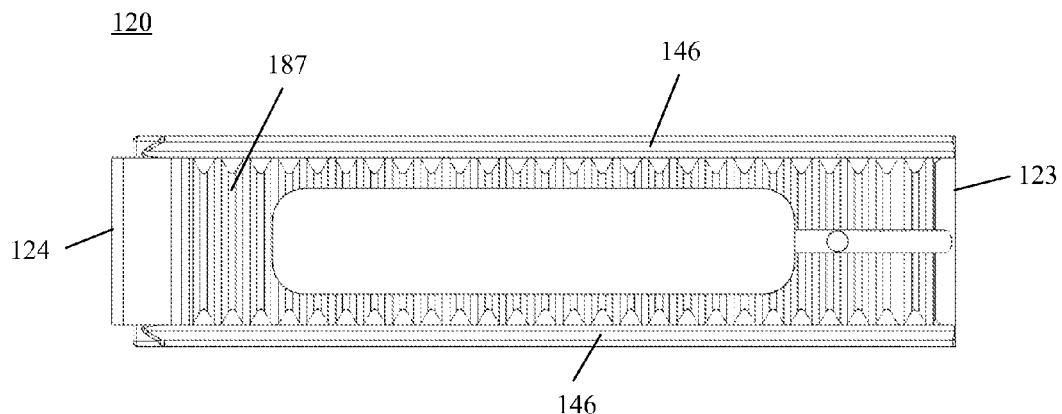
FIG. 9 is a top view of the intermediate spacer member for the tissue spacer device of FIG. 1, in accordance with an aspect of the present invention.

FIG. 9 is a top view of the intermediate spacer member 120 and shows the generally rectangular outside perimeter shape of the intermediate spacer member 120. The opposing sided dovetails 146 appear to be parallel to each other, however, each dovetail (right and left sided) may have a slight inward draft angle when moving from the rear side 124 to the front side 123 of the intermediate spacer member 120. An example embodiment of this configuration may include dovetails 146 that are wider at the rear side 124 relative to the front side 123, alternatively this draft configuration may be reversed.

Figure 10:
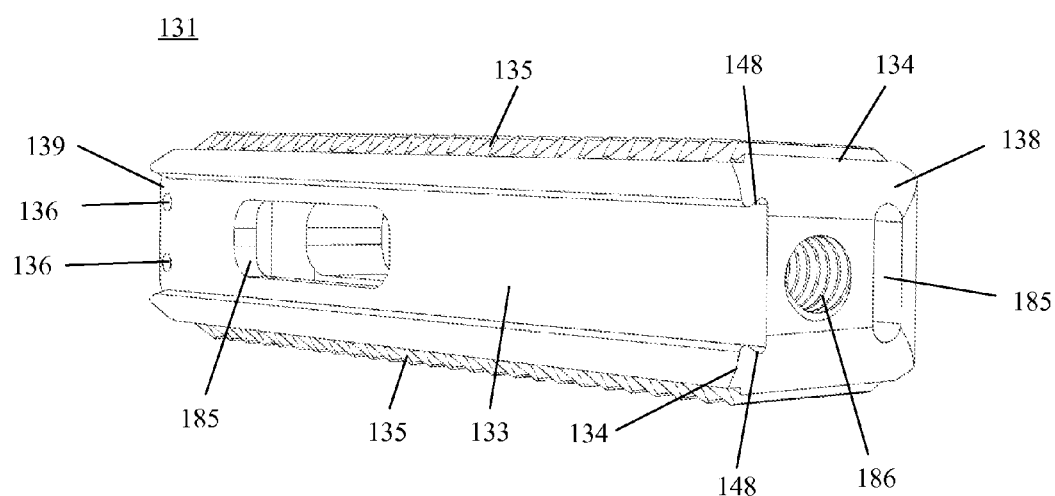
FIG. 10 is a medial side, perspective view of one embodiment of a lateral member of the tissue spacer device of FIG. 1, in accordance with an aspect of the present invention.
Figure 11:
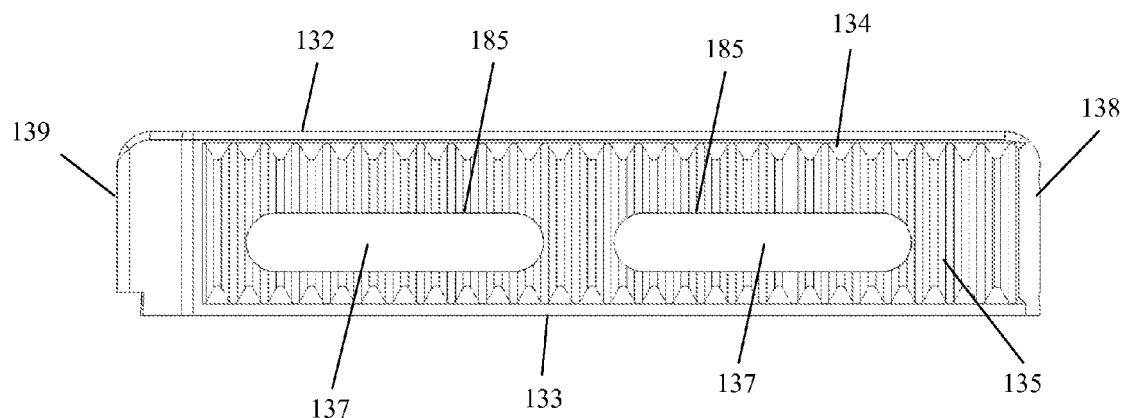
FIG. 11 is a top view of the lateral member of the tissue spacer device of FIG. 1, in accordance with an aspect of the present invention.
Figure 12:
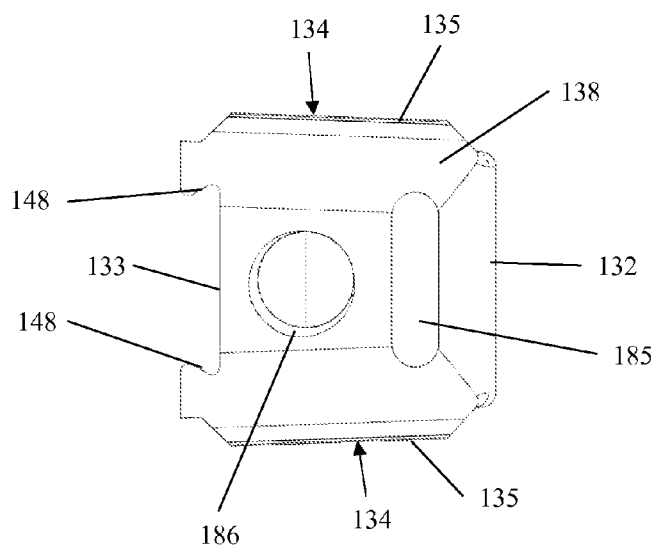
FIG. 12 is a front, elevational view of the lateral member of the tissue spacer device of FIG. 1, in accordance with an aspect of the present invention.

FIGS. 10-12 show the lateral member 131, which may be a mirror image of lateral member 130, and the lateral members 130, 131 may be movingly attached to both sides of the intermediate spacer member 120. The lateral members 130, 131 may be mirror images of each other when the two are positioned on either side of the intermediate spacer member 120. The lateral members 130, 131 may have the same height and have parallel and planar bone contacting surfaces 135. However, if the implant 100 is used to correct angular deformities, the bone contacting surfaces 135 of the two lateral members 130, 131 may be angled and the overall heights of each of the two lateral members 130, 131 may be different. An example of this configuration is shown in FIG. 1. As seen in FIG. 11, the outer profile of the lateral members 130, 131 is generally rectangular, although it is contemplated that other shapes and configurations may be used depending on the clinical situation.

Generally, as seen in FIG. 10, the lateral members 130, 131 include top and bottom bone contacting surfaces 135. As also seen in FIG. 10, similar to the top and bottom bone contacting surfaces 187 of the intermediate spacer member 120, the bone contacting surfaces 135 for the lateral members 130, 131 are generally parallel to each other (see FIG. 12). Further as seen in FIGS. 5-10 and 11, the bone contacting surfaces 135 and 187 may have a roughened surface that includes teeth-like or tine structures projecting away from the superior and inferior surfaces. One skilled in the art would recognize that other surface treatments may be applied to the bone contacting surfaces 135, 187 to enhance fixation with the opposing bone surface, but not limited to sharp tines, porous coatings, nano-coatings, bio-active/ingrowth surfaces, ridge structures, and the like. Further, it is contemplated that angled bone contacting surfaces, caps or plates may be attachable to the lateral members 130, 131 to address various skeletal deformities that are encountered clinically. It is also understood that the bone contacting surfaces of such modular surfaces, caps or plates may include various bioactive or bone ingrowth coatings or have a range of surface topography configurations.

As shown in FIGS. 10-12, the lateral members 130, 131 also may include a central cavity 137 that is defined by the top and bottom sides 134, an inner side 133, an outer side 132, a front side 138, and a rear side 139. The cavity 137 may be divided by one or more walls to create multiple cavities 137, for example, as shown in FIG. 11 there are two cavities 137. The front side 138 also includes numerous openings 185 including a threaded hole 186. The numerous openings 185 are also disposed on the rear side 139, the outer side 132 and the inner side 133. Further, as seen in FIG. 11, several openings 185 are disposed on the top and bottom sides 134 to allow for the packing of bone graft material within the cavity 137.

As shown in FIGS. 10 and 12, the inner side 133 includes a pair of female dovetails 148 that are configured to slide onto the male dovetails 146 of the intermediate spacer member 120. The dovetails 146, 148, in combination, slidingly attach the lateral members 130, 131 to the intermediate spacer member 120. Located adjacent to the rear side 139 are two openings 136 which may include two posts or projections (not shown) which slide into a corresponding notch 184 in the intermediate spacer member 120 as the intermediate spacer member 120 is moved in a front to rear direction. For example purposes, two openings 136 are shown in FIGS. 10 and 12, although it is understood that fewer or more openings 136 for posts and other configured stopping projections may be used. The posts may function to securely position the lateral members 130, 131 relative to the intermediate spacer member 120 prior to actuation of the coupling mechanism 150.

Figure 13:
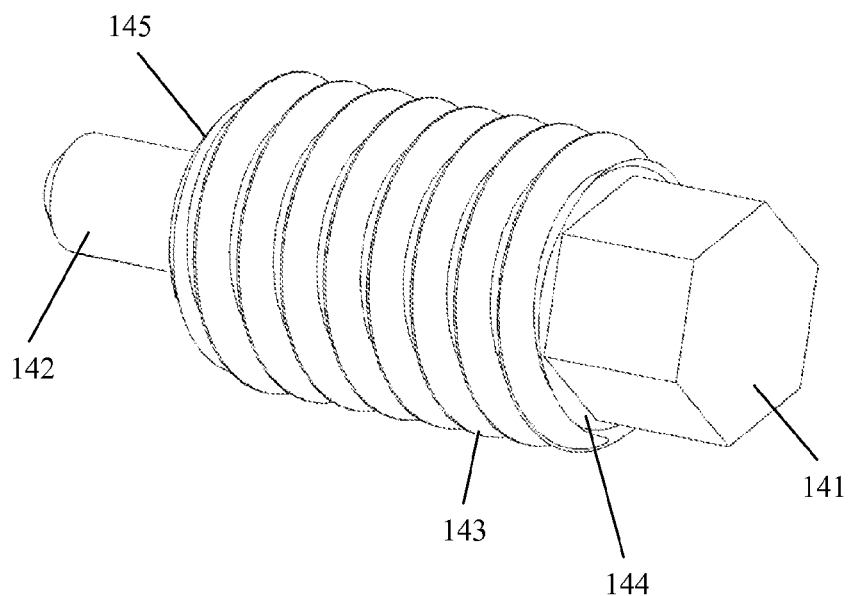
FIG. 13 is a side, perspective view of a threaded rod of the coupling mechanism of the tissue spacer device of FIG. 1, in accordance with an aspect of the present invention.
Figure 14:
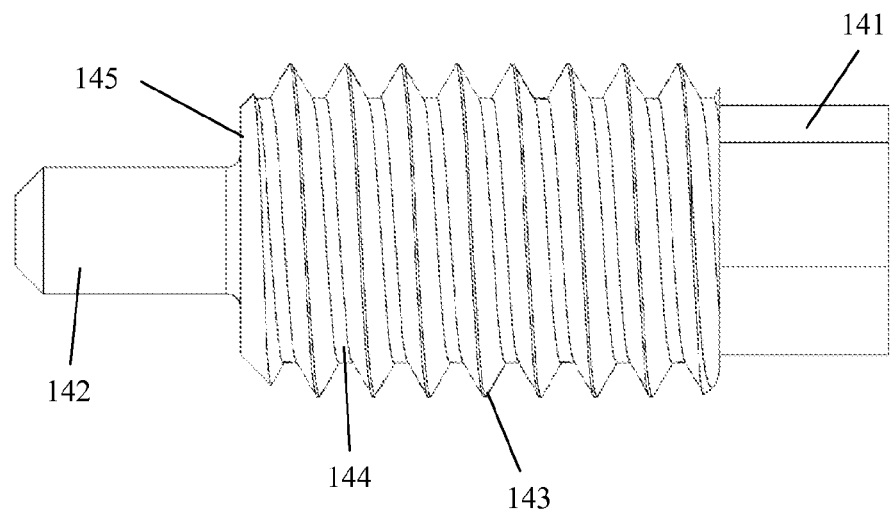
FIG. 14 is a side, elevational view of the threaded rod of the coupling mechanism of the tissue spacer device of FIG. 1, in accordance with an aspect of the present invention.

A threaded rod or screw 140 is shown in FIGS. 13 and 14. The rod 140 includes a head portion 141, threads 143 and a projection or extension 142. The head portion 141 may be, for example, a hex head, as shown, although other multi-lobed configurations may be used depending on the tightening tool that is used. Alternatively, it is contemplated that a hex opening or other shaped orifice may be disposed on the head portion 141 for attaching to a drive tool that is used to thread the rod 140 into the front hole 127 of the intermediate spacer member 120. On the opposite end of the threaded rod 140 from the head portion 141 is a projection 142, which may be, for example, circular, and that extends away from a bearing end 145 along the longitudinal axis of the threaded shaft 144. The projection 142 has a smaller diameter than the threaded shaft 144 and has, for example, a circular cross-sectional geometry although other shapes may be used. The projection 142 is also sized to fit into the front hole 113 of the spacer insert 110.

The implant 100 and its modular members may be fabricated from metal, for example, stainless steel, or titanium, among other metals, or non-metallic, for example, high molecular weight (UHMWPE) polyethylene, or its equivalent, polymers or composites, for example PEEK.

Figure 15:
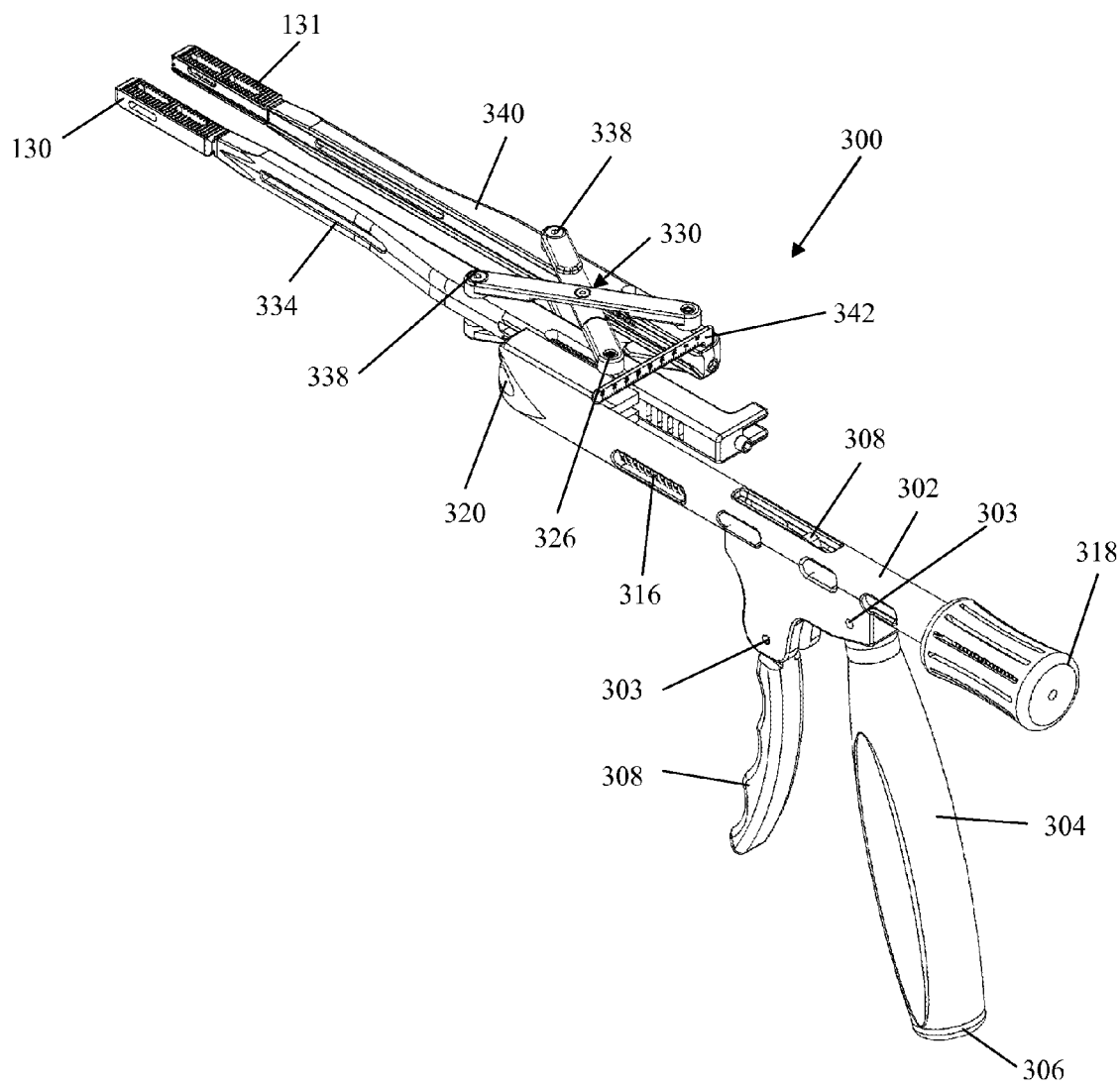
FIG. 15 is a rear, perspective view of an insertion tool for the tissue spacer device of FIG. 1, in accordance with an aspect of the present invention.
Figure 16:
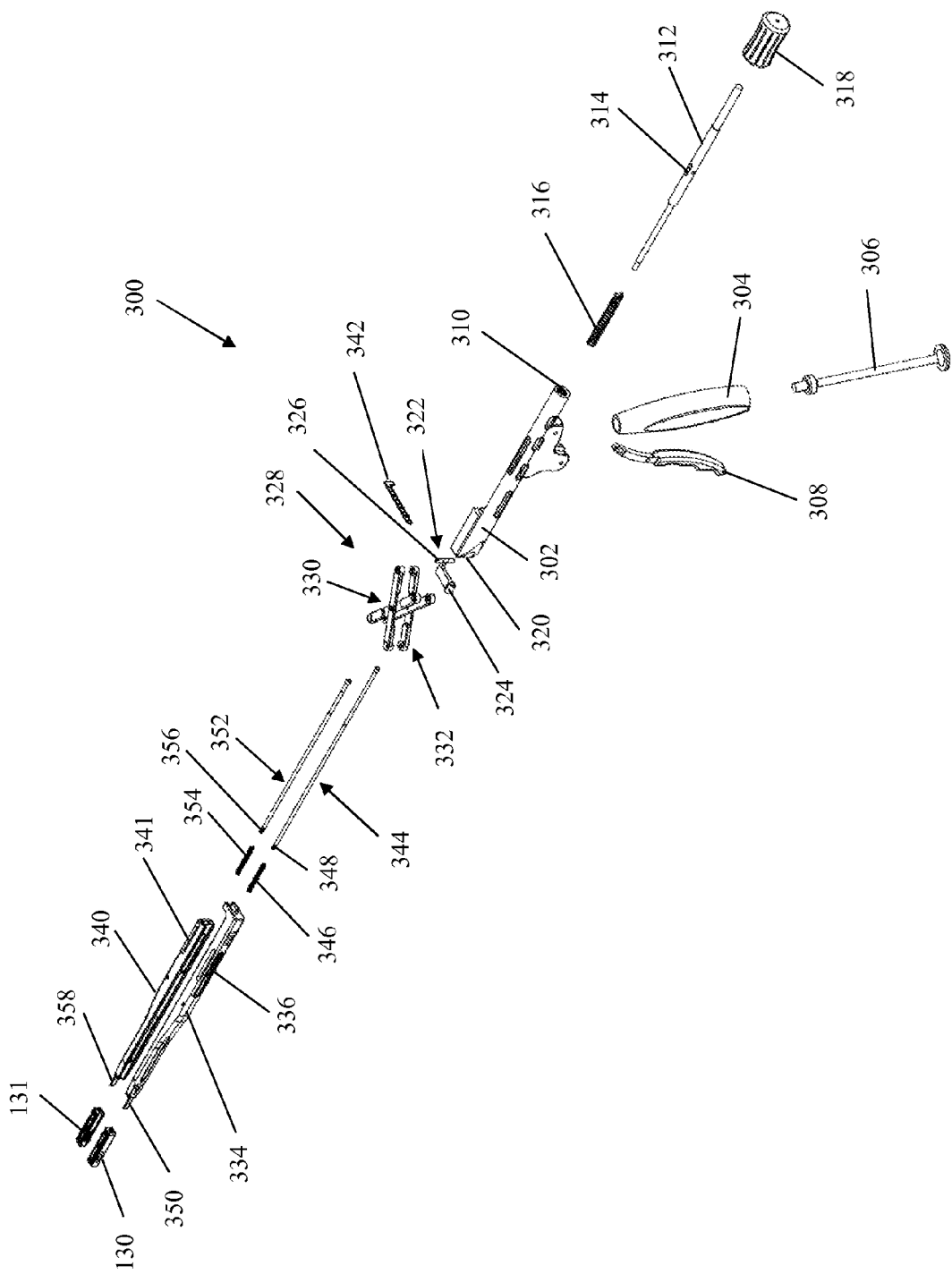
FIG. 16 is an exploded view of the insertion tool of FIG. 15, in accordance with an aspect of the present invention.
Figure 17:
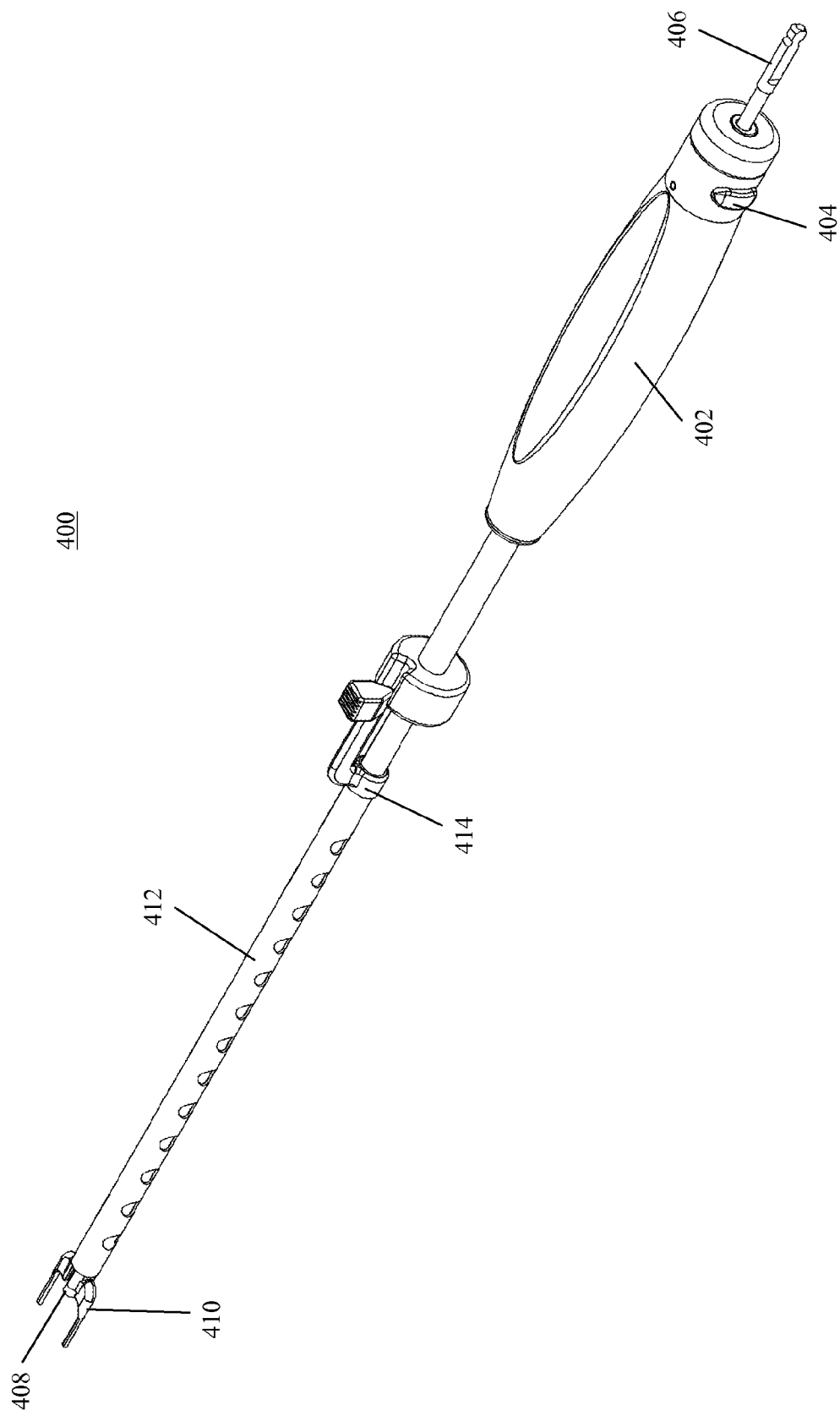
FIG. 17 is an rear, perspective view of another insertion tool for the tissue spacer device of FIG. 1, in accordance with an aspect of the present invention.

For example purposes, when the implant 100 is in use, typically the operating surgeon will use an insertion tool or instrument 300 to which the two lateral members 130, 131 are attached, as shown in FIGS. 15-16 and discussed in greater detail below. The tool 300 will be inserted into the space between two pieces of tissue and adjusted to ensure the proper spacing required between the two lateral members 130, 131 to address the clinical need of the patient. Once the spacing is finalized, the appropriate sized intermediate spacer member 120 is movably attached to a second tool 400, as seen in FIG. 17 and discussed in greater detail below, and placed between the two lateral members 130, 131. As discussed above, the two sets of dovetails 146 on the intermediate spacer member 120 are aligned with the corresponding dovetails 148 of the two lateral members 130, 131 and then the intermediate spacer member 120 is moved in a front to rear direction until the notches 184 come in contact and nest with the corresponding posts inserted into openings 136.

Once the lateral members 130, 131 and the intermediate spacer member 120 are slid together, the coupling mechanism 150 may be actuated. The coupling mechanism 150, as shown in FIGS. 1 and 2, may include the dovetails 146, 148, the spacer insert 110 with the bullet end 112 including the angle segments 115, the intermediate spacer member 120 including the rear opening 128 with the angled portions 182, and the threaded rod 140. The coupling mechanism 150 is actuated by inserting or threading the threaded rod 140 into the threaded hole 127. The projection 142 aligns and slides into the front hole 113 of the spacer insert 110 with the bearing end 145 making contact with the planar wall 111 and causing the spacer insert 110 to move in a rearward direction. As the spacer insert 110 moves, the angled segments 115 of the bullet end 112 make contact with the corresponding angle portions 182 of the tapered opening 128 of the intermediate spacer member 120. As the spacer insert 100 continues to move in a rearward direction, the two angled segments 115 of the bullet end 112 slide along and up the angled incline of the angled portions 182 causing the side slots 125 to open, increase, or widen, the top and bottom walls 129, 181 to move away from each other, and the two sets of integral dovetails 146 of the intermediate spacer member 120 to come in pressing contact with the stationary dovetails 148 of the two lateral members 130, 131 to lock the three members 130, 120, 131 together. The tool 300 may also be used as a distraction instrument to remove the implant 100 from a patient by reversing the above noted insertion method.

As shown in FIGS. 15 and 16, the tool 300 includes a body 302 with a handle portion 304 coupled to the body 302 by a securement mechanism 306. The body 302 may also be moveably coupled to a trigger 308 which may be positioned proximal the handle portion 304 on a bottom side of the body 302. The handle portion 304 and the trigger 308 may be coupled to the body 302 using one or more fasteners 303, for example, screws, pins, rivets and the like. The body 302 may also include a distal opening 310 for receiving a rod 312 which includes an opening 314. The rod 312 may also include a spring 316 inserted over a portion of the proximal end of the rod 312 and a knob 318 attached to the distal end of the rod 312. The assembled rod 312, spring 316, and knob 318 may be inserted into the distal opening 310 enabling the trigger 308 to couple to the rod 312 through the opening 314. In addition, the proximal end of the rod 312 may engage the actuation mechanism 322 which is inserted through the proximal opening 320 of the body 302.

The actuation mechanism 322 may include a first portion 324 and a second portion 326, as seen in FIG. 16. The first portion 324 is slidingly inserted into the opening 320 to couple to the rod 312 and the second portion 326 couples to the translation or scissor mechanism 328. The second portion 326 of the actuation mechanism 322 may also slidingly engage an opening 336 in a first housing 334 prior to engaging the scissor mechanism 328. The first housing 334 may be coupled to the body 302 on the proximal end. The translation or scissor mechanism 328 includes a first hinged pair of top supports 330 and a second hinged pair of bottom supports 332. The second portion 326 of the actuation mechanism 322 may couple to one end of one of the top supports 330 and the corresponding end of one of the bottom supports 332. The side of the scissor mechanism 328 which is coupled to the actuation mechanism 322 may also be coupled to the first housing 334. As shown in the depicted embodiment, the proximal end of the left side of the scissor mechanism 328 may be rotatably coupled to the first housing 334 using at least one fastener 338, for example, a screw, pin, or the like. The proximal end of the right side of the scissor mechanism 328 may be rotatably coupled to a second housing 340 using at least one fastener 338. In addition, the distal end of the right side of the scissor mechanism 328 may be slidingly coupled to the second housing 340 through opening 342 using, for example, a pin member. As shown in FIG. 15, the trigger 308 is coupled to the actuation mechanism 322 which is in turn coupled to the scissor mechanism 328 and the scissor mechanism 328 is coupled to the first and second positioning mechanisms 344, 352. The scissor mechanism 328 is used to convert the proximal-distal translation of the actuation mechanism 322 into horizontal expansion or translation of the housings 334, 340 which are coupled to the lateral members 130, 131.

With continued reference to FIGS. 15 and 16, a measuring device 342 may be coupled to the second housing 340 at the distal end to measure the distance between the first housing 334 and the second housing 340, which in turn provides the measurement of the distance between the lateral members 130, 131. A first positioning mechanism 344 may couple with a spring 346 for insertion into the first housing 334. The proximal end 348 of the first positioning mechanism 344 is configured to engage a lateral member 130 and may extend out of the proximal end of the first housing 334 to couple to the lateral member 130. The first housing 334 may also include an alignment protrusion 350 for engaging the lateral member 130 for attachment of the first positioning mechanism 344 prior to insertion of the implant 100 into the patient. Similarly, a second positioning mechanism 352 may couple with a spring 354 for insertion into the second housing 340. The proximal end 356 of the second positioning mechanism 352 is configured to engage a lateral member 131 and may extend out of the proximal end of the second housing 340 to couple to the lateral member 131. The second housing 340 may also include an alignment protrusion 358 for engaging the lateral member 131 for attachment of the second positioning mechanism 352 prior to insertion of the lateral members 130, 131 into the patient.

The second insertion tool 400 for the implant 100 is shown in FIG. 17. The second tool 400 includes a handle 402 with an actuation mechanism 404. The actuation mechanism 404 is configured to enable the engagement shaft 406 to be secured in a first position wherein the implant 100 is secured to the proximal end 408 of the engagement shaft 406 for insertion into a patient and then upon actuation of the actuation mechanism 404 the engagement shaft 406 may be moved to a second position in order to remove the tool 400 leaving a intermediate spacer member 120 of the implant 100 in the patient. The tool 400 may also include an alignment head 410 for alignment of the intermediate spacer member 120 on the tool 400 for insertion into the patient. The tool 400 may further include a moveable housing 412 coupled to a tab 414 to assist in the alignment and insertion of the intermediate spacer member 120 between two lateral members 130, 131.

Figure 18:
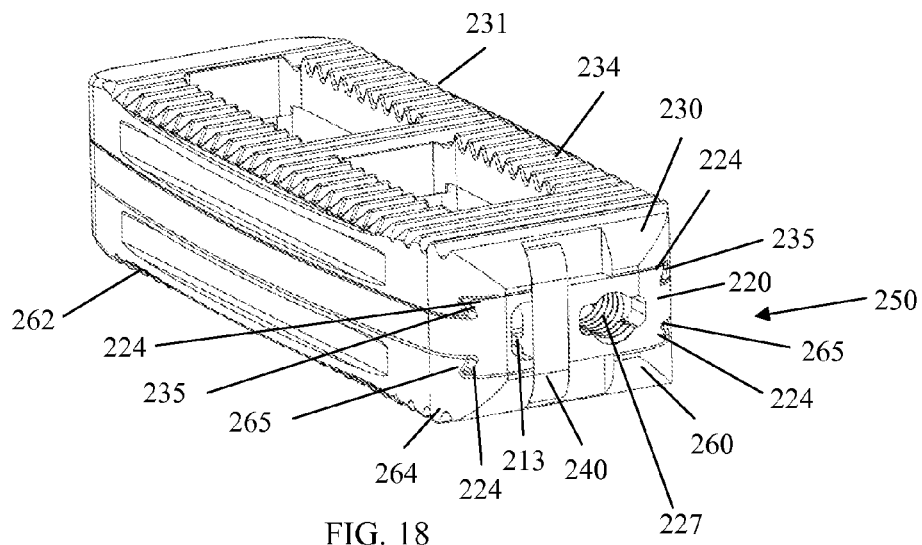
FIG. 18 is a front, perspective view of one embodiment of a vertical expandable tissue spacer device, in accordance with an aspect of the present invention.
Figure 19:
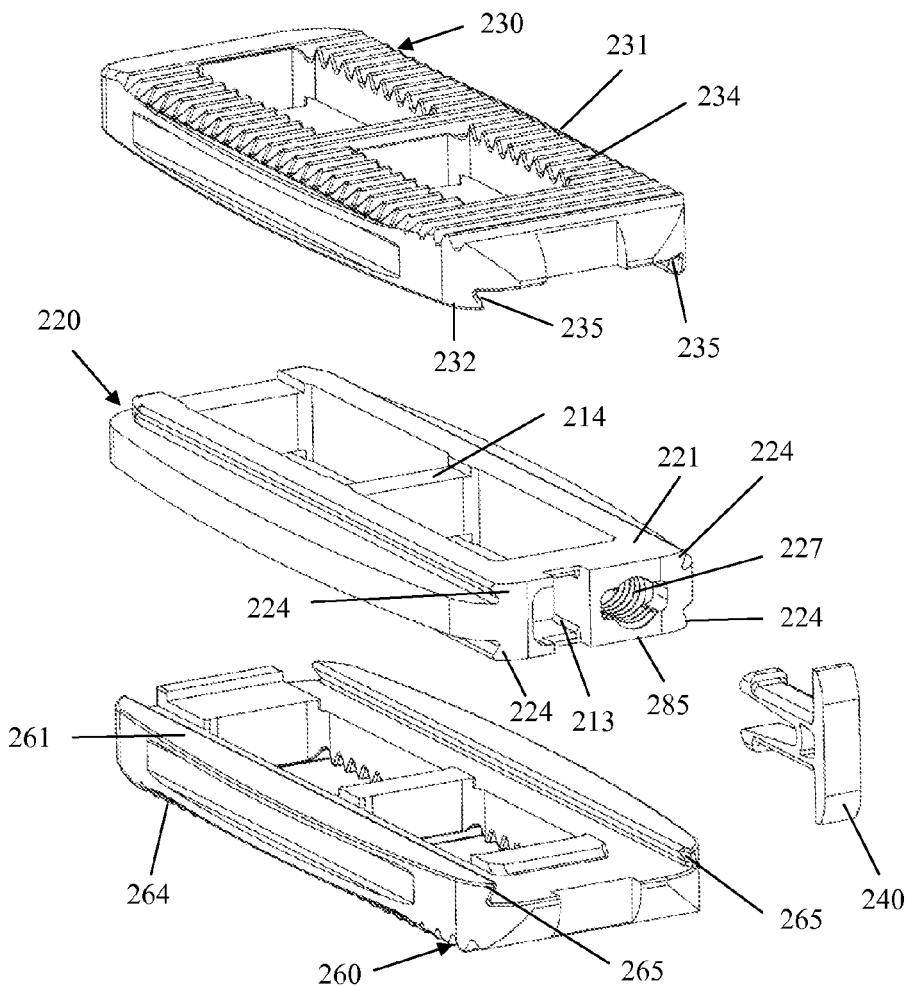
FIG. 19 is an exploded front, perspective view of the tissue spacer device of FIG. 18, in accordance with an aspect of the present invention.

FIGS. 18 and 19 show another embodiment of a tissue spacer implant. According to aspects of the invention, a vertical tissue spacer implant 200 includes an intermediate spacer member 220 positioned between a top member 230 and a bottom member 260. The intermediate spacer member 220 includes a top side 221 and a bottom side 285 opposite the top side 221. The intermediate spacer member 220 typically includes at least two pairs of dovetails 224 disposed on the top side 221 and the bottom side 285 adapted to couple the bottom surface 232 of the top member 230 and the top surface 261 of the bottom member 260, respectively. The top member 230 and the bottom member 260 may be modular and allow the surgeon to mix and match various shaped, sized, and configured members 230, 260 chosen from a kit with the intermediate spacer member 220. The kit may include a plurality of different sized members 220, 230, 260 enabling the surgeon to select the necessary components for insertion into each specific patient.

For example purposes, FIG. 18 shows the implant construct to have planar top and bottom surfaces, although these surfaces for some embodiments may be angled. As seen in FIG. 18 for this example of the implant 200, the top surface 231 of the top member 230 is planar and the bottom surface 262 of the bottom member 260 is also planar. In alternative embodiments, the top surface 231 may be, for example, angled from left to right and the bottom surface 262 may be, for example, angled from left to right. It is understood that the angulations of the top and bottom surfaces 231, 262 may also be reversed or, alternatively, both the top surface 231 and the bottom surface 262 could be straight. If the bone contacting surfaces 234, 264 of the implant 200 are angled, the implant 200 may be used to correct deformities in vivo.

FIG. 19 is an exploded view showing the other elements that comprise the vertical tissue spacer implant 200. The implant 200 may include the intermediate spacer member 220 and a locking mechanism 240 which may couple to the intermediate spacer member 220. The locking mechanism 240 may be inserted through an opening 213 in the intermediate spacer member 220. As will become clear when discussing the aspects of the invention, in one aspect, the top member 230 and the bottom member 260 may be positioned adjacent to the top and bottom margins of a space that exists between two tissue parts (not shown), for example, bone, whereby the intermediate spacer member 220 may be inserted between the top member 230 and the bottom member 260. During or after insertion of the intermediate spacer member 220 between the top member 230 and the bottom member 260, a coupling mechanism 250 may be actuated to attach the three components 220, 230 and 260 together as the implant 200. According to aspects of the invention, the coupled members 220, 230 and 260 provide a substantially rigid implant between adjacent tissues, for example, vertebrae. In one aspect of the invention, the intermediate spacer member 220 may be provided in a kit that includes a plurality of widths or heights, whereby the intermediate spacer member 220 may be selected from the kit which includes one of these various sizes of intermediate spacer members 220 depending upon the spacing needed between the top member 230 and the bottom member 260. Various sizes of the top member 230 and the bottom member 260 may also be components of the kit.

Figure 20:
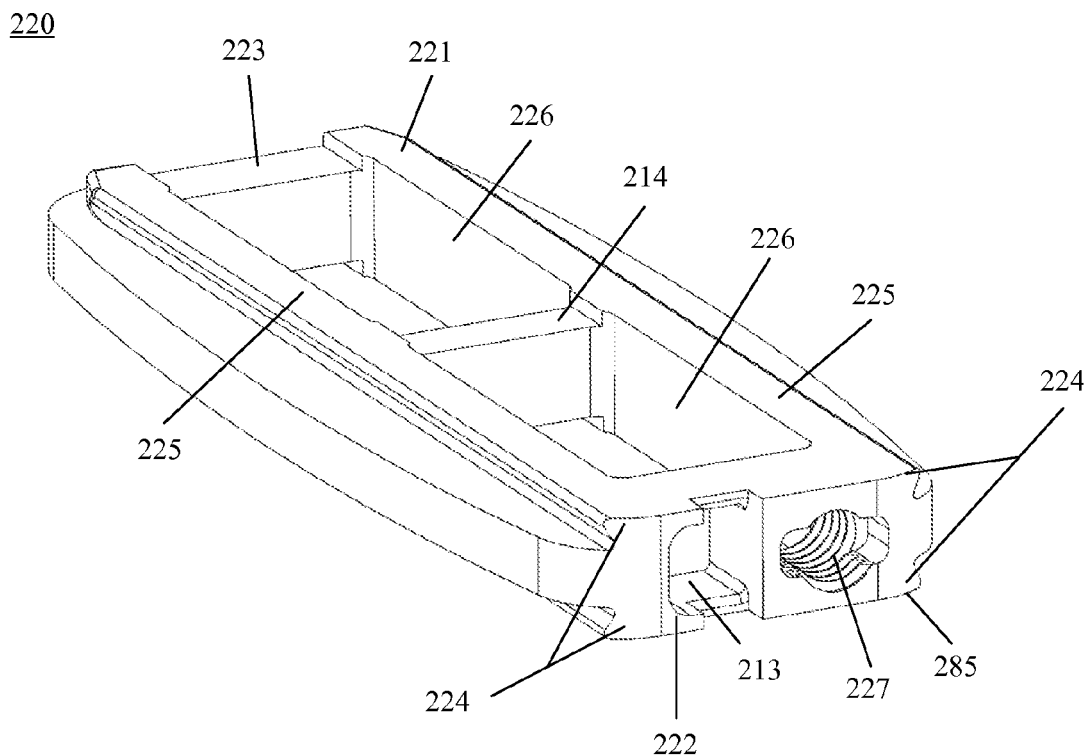
FIG. 20 is a front, perspective view of an intermediate spacer member for the tissue spacer device of FIG. 18, in accordance with an aspect of the present invention.
Figure 21:
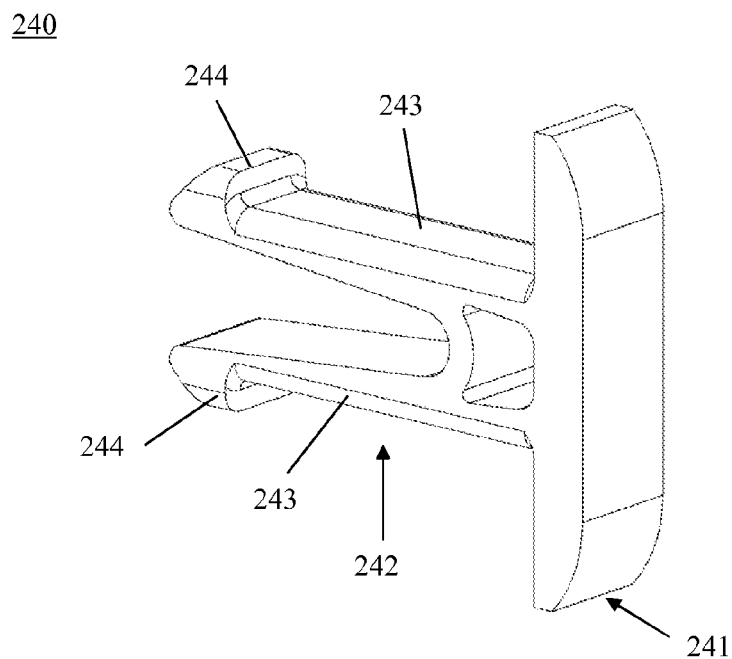
FIG. 21 is a front, perspective view of a locking mechanism for the tissue spacer device of FIG. 18, in accordance with an aspect of the present invention.

Seen in FIG. 20 is the intermediate spacer member 220. The intermediate spacer member 220 includes two openings 226 that extend through the center and are separated by a central wall 214. The openings 218 are sized to allow the surgeon to pack bone grafting material into and through the entire implant 200. The intermediate spacer member 220 also includes a threaded hole 227 and an opening 213. The threaded hole 227 is located at one end and offset from the midline of the front wall 222 and the opening 213 is located at the same end as and offset from the midline on a side opposite the threaded hole 227 on the front wall 222. The opening 213 is sized to receive the tip or extension 242 of the locking mechanism 240, as seen in FIG. 21. A rear wall 223 is opposite the front wall 222. The openings 226 also have two side walls 225 that define the length of the implant 200. The generally rectangular outside perimeter shape of the intermediate spacer member 220 is seen in FIG. 20.

A locking mechanism 240 is seen in FIG. 21. The locking mechanism 240 includes a head portion 241 and an extension portion 242. The head portion 241 may engage a portion of the front wall 222 when inserted into the opening 213. The extension portion 242 may include at least one leg 243 and a protrusion 244 on each leg 242. In the illustrated embodiment there are, for example, two legs 243 each including a protrusion 244. The legs 243 expand after insertion into the opening 213 to engage the top member 230 and the bottom member 260.

Figure 22:
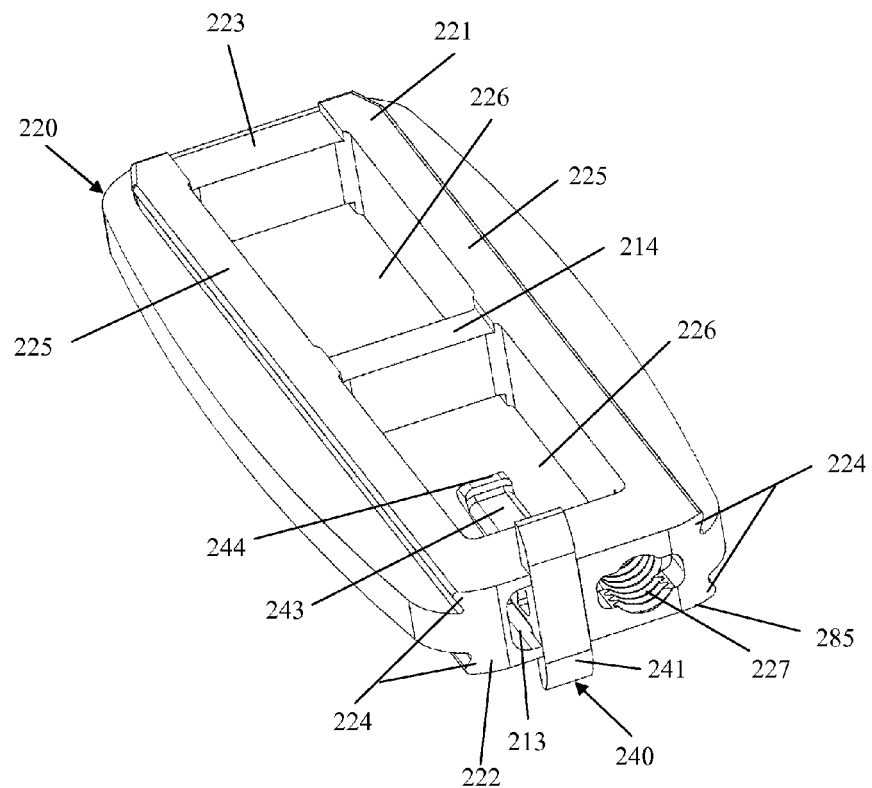
FIG. 22 is a front perspective view of the intermediate spacer member with the locking mechanism in position for the tissue spacer device of FIG. 18, in accordance with an aspect of the present invention.

Also seen in FIGS. 20 and 22 are part of the elements of the coupling mechanism 250, specifically, the longitudinal female dovetails 224 positioned on the outer sides of the side walls 225 of the intermediate spacer member 220. The opening 213 is also an element of the coupling mechanism 250. The two sets of dovetails 224 that are located on the outer surfaces of the two opposing side walls 225 are generally parallel to each prior to insertion of the locking mechanism 240. When the locking mechanism 240 is inserted into opening 213, the locking mechanism 240 is moved in a rearward direction (towards rear wall 223) causing the protrusions 244 to flex toward each other. As the locking mechanism 240 is moved rearward, the protrusions 244 enter the central cavities 237, 267 of the top and bottom members 230, 260. The protrusions 244 are able to snap outward, resulting in the capturing and securement of the top and bottom members 230, 260 to the intermediate spacer member 220. The locking mechanism 240 may be made of a deformable or elastic material to enable deformation for insertion and removal. In an alternative embodiment, the top aspect and bottom aspect of the rear wall 223 may include, for example, four notches (not shown) that are sized to receive corresponding posts (not shown) of the top member 230 and bottom member 260 respectively. The notches may facilitate holding the top and bottom members 230, 260 in a constant position relative to the dovetails 224 when the intermediate spacer member 220 is slid between them.

Figure 23:
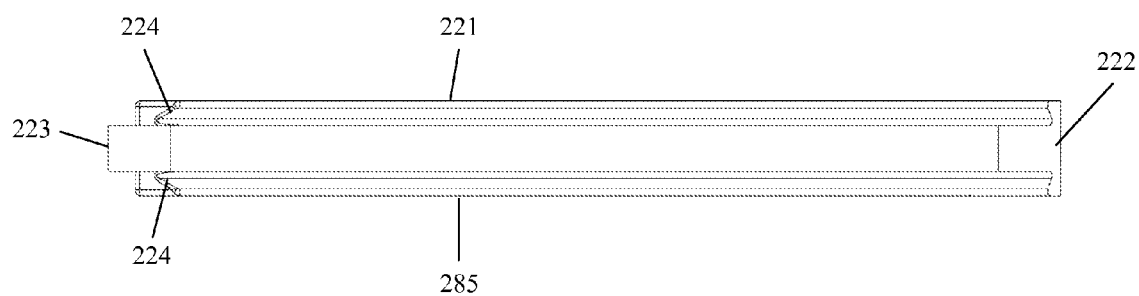
FIG. 23 is a side, elevational view of the intermediate spacer member without the locking mechanism in position for the tissue spacer device of FIG. 18, in accordance with an aspect of the present invention.

FIG. 23 is a side view of the intermediate spacer member 220. This view shows one pair of the dovetails 224 and the parallel relationship between the upper element of the dovetail 224 relative to the lower element of the dovetail 224. The planar configuration of the top and bottom sides 221, 285 is also seen.

Figure 24:
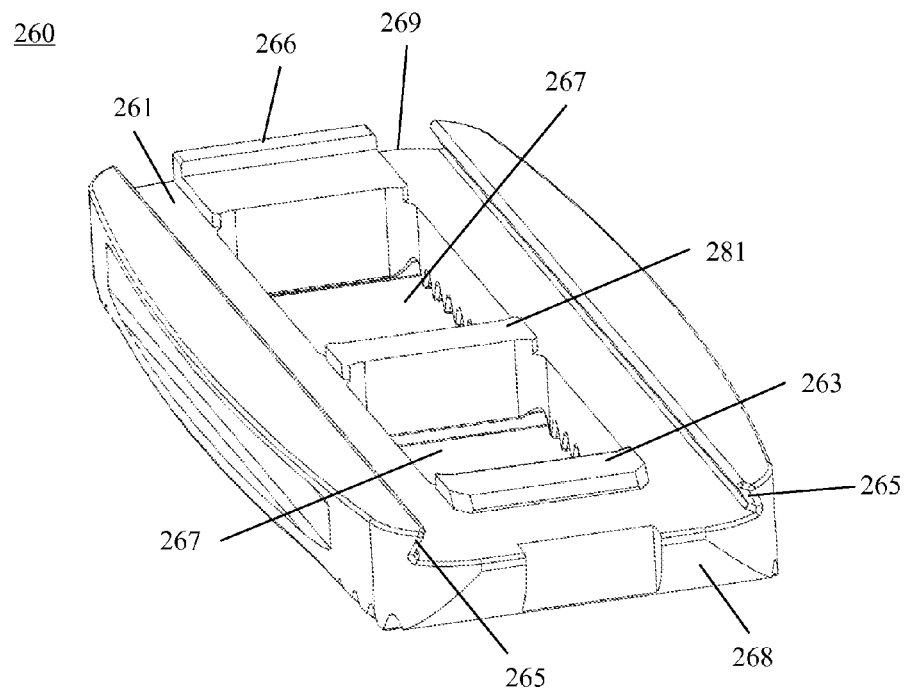
FIG. 24 is a front, perspective view of one embodiment of a bottom member of the tissue spacer device of FIG. 18, in accordance with an aspect of the present invention.
Figure 25:
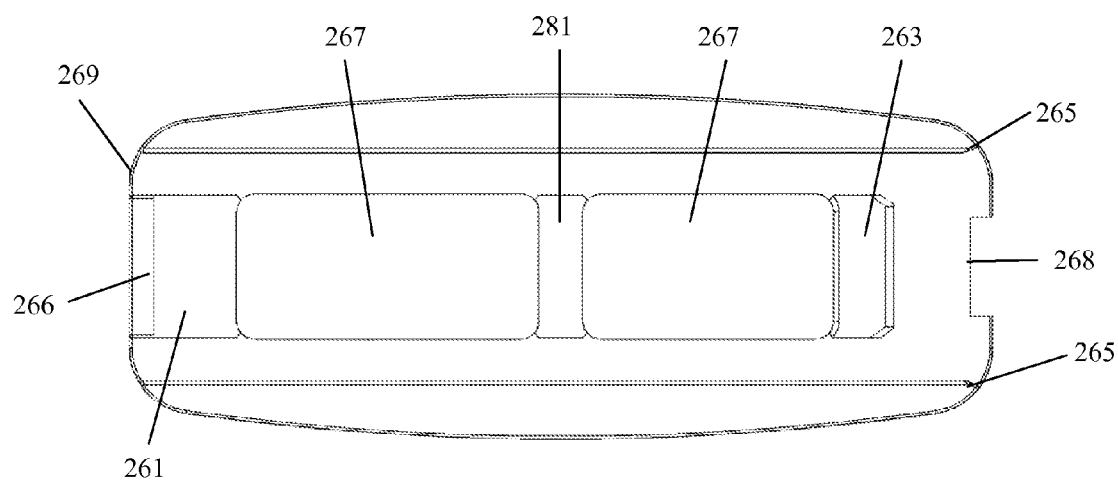
FIG. 25 is a top view of the bottom member of the tissue spacer device of FIG. 18, in accordance with an aspect of the present invention.
Figure 26:
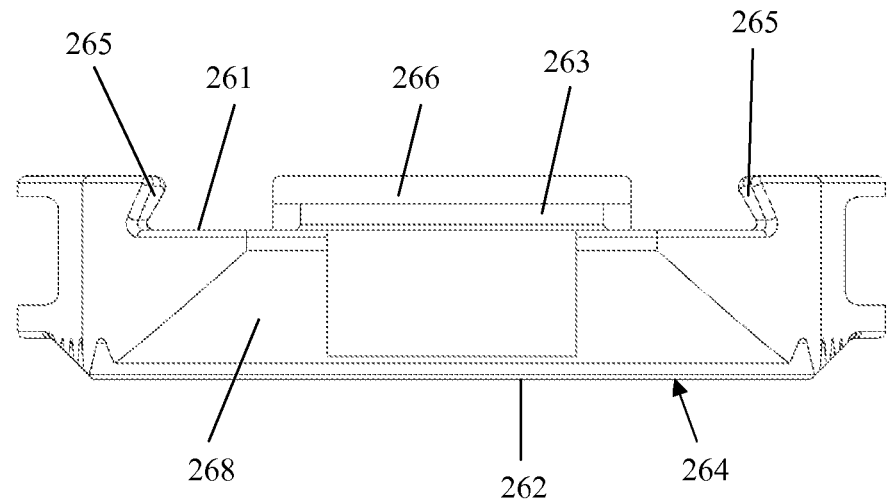
FIG. 26 is a front, elevational view of the bottom member for the tissue spacer device of FIG. 18, in accordance with an aspect of the present invention.

FIGS. 24-26 show the bottom member 260 that is movingly attached to the bottom side 285 of the intermediate spacer member 220. For brevity sake, only the bottom member 260 will be described as the top member 230 is a mirror image and has the same structural elements. These can be seen in comparing FIG. 26 (bottom member 260) to FIG. 27 (top member 230).

Generally, as seen in FIG. 18, the top and bottom members 230, 260 include a bone contacting surface 234, 264. As seen in FIG. 18, the bone contacting surfaces 234, 264 for the top and bottom members 230, 260 are generally parallel to each other and are either angled or straight. Further, the bone contacting surfaces 234, 264 may have a roughened surface that includes teeth-like or tine structures projecting away from the superior and inferior surfaces. One skilled in the art would recognize that other surface treatments may be applied to the bone contacting surfaces 234, 264 to enhance fixation with the opposing bone surface, but not limited to sharp tines, porous coatings, nano-coatings, bio-active/ingrowth surfaces and ridge structures. Further, it is contemplated that the bone contacting surfaces, caps or plates may be attachable to the top and bottom members 230, 260 to allow for modular components to address various skeletal deformities that are encountered clinically. It is also understood that the bone contacting surfaces of such modular surfaces, caps or plates may include various bioactive or bone ingrowth coatings or have a range of surface topography configurations.

As seen in FIGS. 24 and 25, the bottom member 260 also may include at least one central cavity 267 that is defined by the front wall 268 and the back wall 269. A middle wall 281 may divide the cavity 267 into two separate cavities. The cavity 267 allows the surgeon to pack bone graft material through the implant 200.

As shown in FIGS. 24 and 26, the top surface 261 includes a pair of male dovetails 265 that are configured to be aligned and slid into the corresponding female dovetails 224 of the intermediate spacer member 220. The dovetails 265, 235, and 224, in combination, couple the bottom member 260, the top member 235 respectively, to the intermediate spacer member 220.

Figure 27:
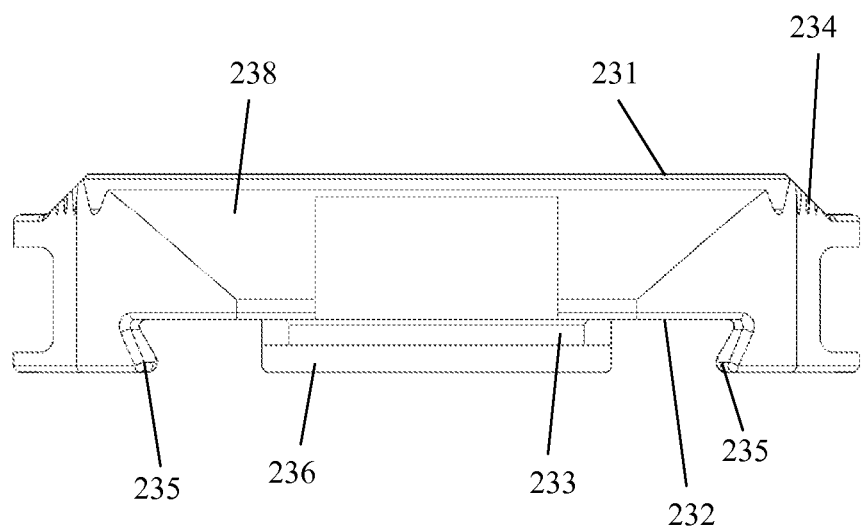
FIG. 27 is a front, elevational view of the top member for the tissue spacer device of FIG. 18, in accordance with an aspect of the present invention.

As seen in FIGS. 24-27, located on the bottom surface 232, top surface 261 of the back wall 239, 269 is a projection 236, 266 that engages the rear wall 223 of the intermediate spacer member 220 as the intermediate spacer member 220 is moved in a front to rear direction when the implant 200 is assembled in situ. For example purposes, the two projections 236, 266 are shown in FIGS. 24 and 27, although it is understood that there could be multiple projections or other configured stopping projections may be used. The projections 236, 266 function to securely position the top member 230 and the bottom member 260 relative to the intermediate spacer member 220 prior to actuation of the coupling mechanism 250. The projections 236, 266 may also assist in preventing the intermediate spacer member 220 from sliding out the rear end of the top and bottom members 230, 260 during insertion of the intermediate spacer member 220. In addition, the top and bottom members 230, 260 may also include front projections 233, 263 which may assist in positioning the top and bottom members 230, 260 relative to the intermediate spacer member 220.

Each of the edges of the dovetails 235, 265 appear to be straight, however, each dovetail (right and left sided) may have a slight inward draft angle when moving from the rear wall 223 to the front wall 222 of the intermediate spacer member 220. An example embodiment of this configuration may be that the dovetails 235, 265 may be wider at the back wall 239, 269 relative to the front wall 238, 268 or this draft configuration could be reversed. The angled draft may be integrated into the dovetails 235, 265 to ensure maximum contact with the female dovetails 224 of the intermediate spacer member 220 prior to actuation of the coupling mechanism 250.

As seen in FIG. 25, the outer profile of the bottom member 260 (this is the same for the top member 230) is generally rectangular, although it is contemplated that other shapes and configurations may be used depending on the clinical situation.

FIGS. 26 and 27 are front elevational views of the top member 230 (FIG. 27) and the bottom member (FIG. 26). As shown, the bone contacting surfaces 234, 264 are straight. Although not shown, it is contemplated that the bone contacting surfaces 234, 264 may be for example, angled from left to right or in the reverse orientation. Angling the bone contacting surfaces 234, 264 allows the user to utilize the implant 200 to address angular deformities. Also seen is that the bottom surface 232 for the top member 230 and the top surface 261 for the bottom member 260 are flat. This is done to ensure easy assembly with the mating dovetails and maximum load transfer between the three joined components.

For example purposes, when the implant 200 is in use, typically the operating surgeon will use an insertion tool or instrument 500 (See FIGS. 28 and 29) to which top and bottom members 230, 260 are attached. The tool end to which the members are attached will be inserted into the space between the two pieces of tissue and adjusted to ensure the proper spacing required between the two members 230, 260 to address the clinical need is achieved. Once the spacing is finalized, the appropriate sized intermediate spacer member 220 is movably attached to a second insertion tool and slid between the top and bottom members 230, 260. The second insertion tool may be of the type described above with reference to tool 400, although the alignment head 410 may be replaced with an alternative alignment head configured to mate with the intermediate spacer member 220. As discussed above, the two pairs of dovetails 224 on the intermediate spacer member 220 are aligned with the corresponding pair of dovetails 235 for the top member 230 and the corresponding pair of dovetails 265 for the bottom member 260 and then the intermediate spacer 220 is slid in a front to rear direction until the rear wall 223 comes into contact with the protrusions 236, 266.

Once the intermediate spacer member 220 is slid to join together with the top member 230 and the bottom member 260, the coupling mechanism 250 may be actuated. The coupling mechanism 250 as shown in FIGS. 18 and 19 likely includes the male and female dovetail pairs 224, 235, 265, the intermediate spacer member 220, and the locking mechanism 240. The coupling mechanism 250 is actuated by inserting the locking mechanism 240 into the opening 213. To insert the locking mechanism 240 into the opening 213, the legs 243 of the extension portion 242 are depressed and slide into the opening 213 of the intermediate spacer member 220 until the head portion 241 makes contact with the front wall 211. As the locking mechanism 240 is inserted into the opening 213 the legs 243 and protrusions 244 flex toward each other and once the protrusions extend into the central cavities 237, 267 they snap outward resulting in the capturing and securement of the top and bottom members 230, 260 to the intermediate spacer member 220. When the top and bottom members 230, 260 engage the intermediate spacer member 220 the two pairs of dovetails 235 and 265 of the top and bottom members 230, 260 engage the pair of dovetails 224 of the intermediate spacer member 220. The tool 500 may also be used as a disassembly instrument to remove the implant 200 from a patient by reversing the above noted insertion method.

The implant 200 and its modular members may be fabricated from metal, for example, stainless steel, or titanium, among other metals, or non-metallic, for example, high molecular weight (UHMWPE) polyethylene, or its equivalent, polymers or composites, for example PEEK.

Figure 28:
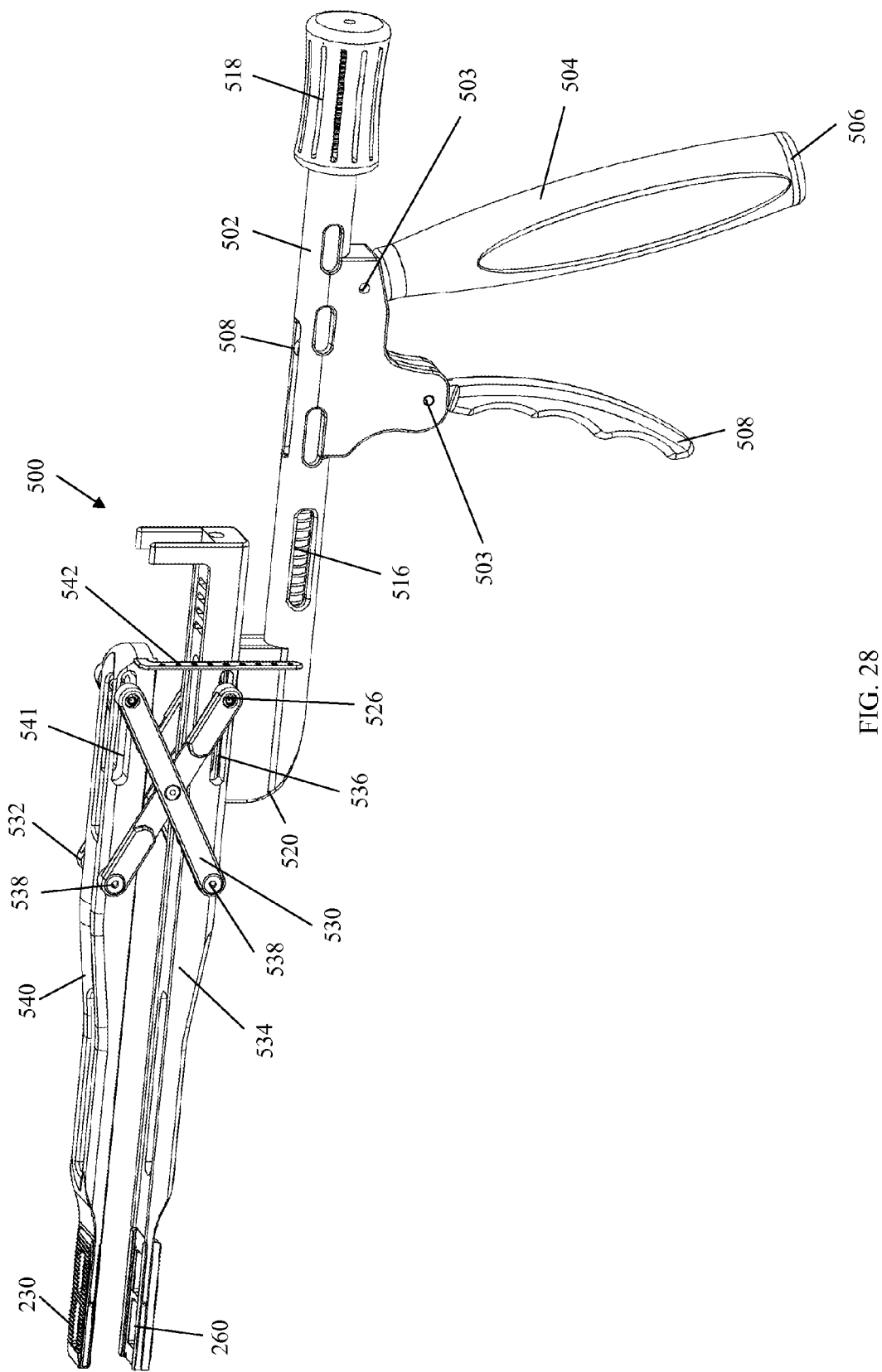
FIG. 28 is a rear, perspective view of an insertion tool for the tissue spacer device of FIG. 18, in accordance with an aspect of the present invention.
Figure 29:
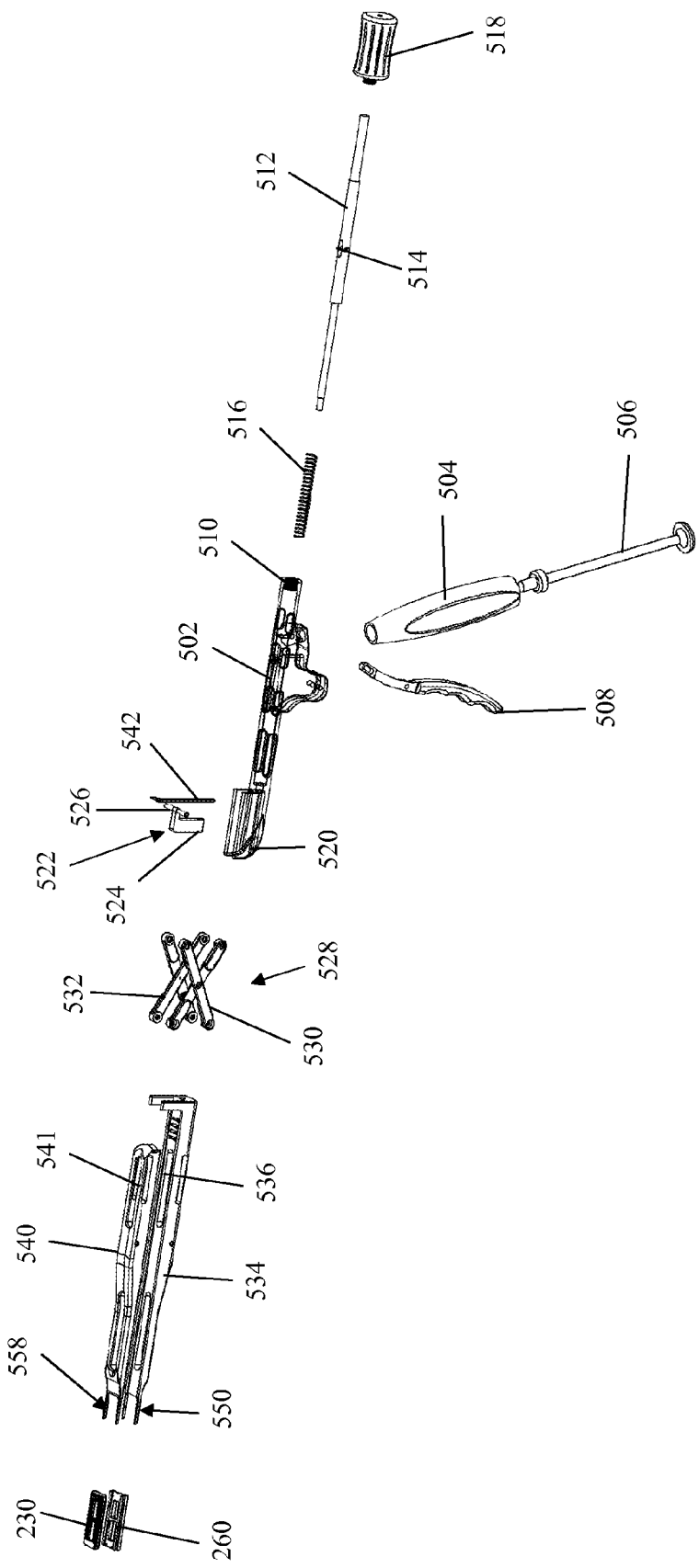
FIG. 29 is an exploded view of the insertion tool of FIG. 28, in accordance with an aspect of the present invention.

FIGS. 28 and 29 show the tool 500, which is similar to the tool 300, as shown in FIGS. 15 and 16, although the tool 500 expands in a vertical direction. The tool 500 includes a body 502, with a handle portion 504 coupled to the body 502 by a securement mechanism 506. The body 502 may also be moveably coupled to a trigger 508 which may be positioned proximal the handle portion 504 on a bottom side of the body 502. The handle portion 504 and the trigger 508 may be coupled to the body 502 using one or more fasteners 503, for example, screws, pins, rivets and the like. The body 502 may also include a distal opening 510 for receiving a rod 512 which includes an opening 514. The rod 512 may also include a spring 516 inserted over a portion of the proximal end of the rod 512 and a knob 518 attached to the distal end of the rod 512. The assembled rod 512, spring 516, and knob 518 may be inserted into the distal opening 510 enabling the trigger 508 to couple to the rod 512 through the opening 514. In addition, the proximal end of the rod 512 may engage the actuation mechanism 522 which is inserted through the proximal opening 520 of the body 502.

The actuation mechanism 522 may include a first portion 524 and a second portion 526, as seen in FIG. 29. The first portion 524 is slidingly inserted into the opening 520 to couple to the rod 512 and the second portion 526 couples to the translation or scissor mechanism 528. The second portion 526 of the actuation mechanism 522 may also slidingly engage an opening 536 in a first housing 534 prior to engaging the scissor mechanism 528. The first housing 534 may be coupled to a proximal end of the body 502. The translation or scissor mechanism 528 includes a first hinged pair of supports 530 and a second hinged pair of supports 532. The second portion 526 of the actuation mechanism 522 may couple to one end of one of the supports 530 and the corresponding end of one of the supports 532. The bottom of the scissor mechanism 528 which is coupled to the actuation mechanism 522 may also be coupled to the first housing 534. As shown in the depicted embodiment, the proximal end of the bottom of the scissor mechanism 528 may be rotatably coupled to the first housing 534 using at least one fastener 538, for example, a screw, pin, or the like. The proximal end of the top of the scissor mechanism 528 may be rotatably coupled to a second housing 540 using at least one fastener 538. In addition, the distal end of the top of the scissor mechanism 528 may be slidingly coupled to the second housing 540 through opening 542 using, for example, a pin member. In the depicted embodiment, the trigger 508 is coupled to the actuation mechanism 522 which is in turn coupled to the scissor mechanism 528 and the scissor mechanism 528 is coupled to the first and second housings 534, 540. The scissor mechanism 528 is used to convert the proximal-distal translation of the actuation mechanism 522 into vertical expansion or translation of the housings 534, 540 which are coupled to the top and bottom members 230, 260.

With continued reference to FIGS. 28 and 29, a measuring device 542 may be coupled to the second housing 540 at the distal end to measure the distance between the first housing 534 and the second housing 540, which in turn provides the measurement of the distance between the top and bottom members 230, 260. The first housing 534 may also include a coupling protrusion 550 for engaging the bottom member 260 prior to insertion of the implant 100 into the patient. Similarly, the second housing 540 may also include a coupling protrusion 558 for engaging the top member 230 for attachment to the second housing 540 for insertion of the top and bottom members 230, 260 into the patient.

Figure 30:
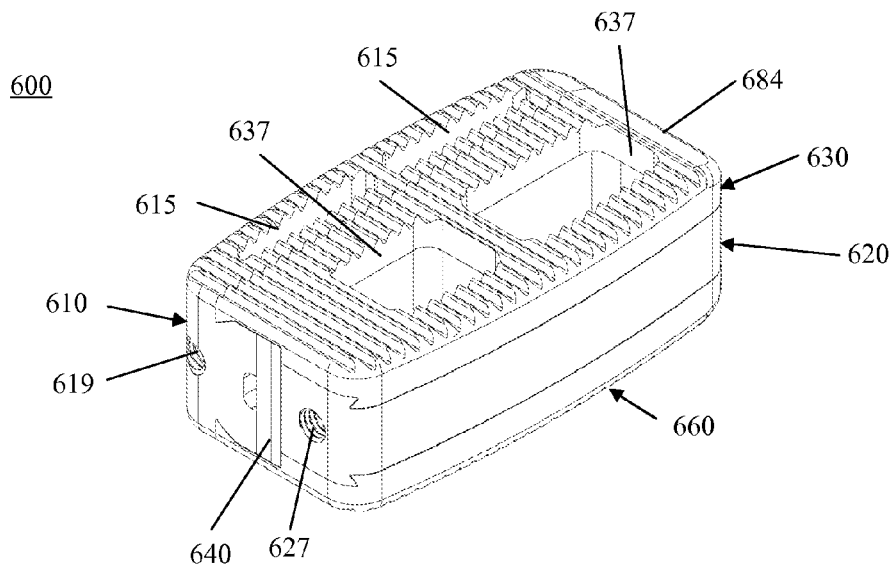
FIG. 30 is a front, perspective view of one embodiment of a vertical and horizontal expandable tissue spacer device, in accordance with an aspect of the present invention.
Figure 31:
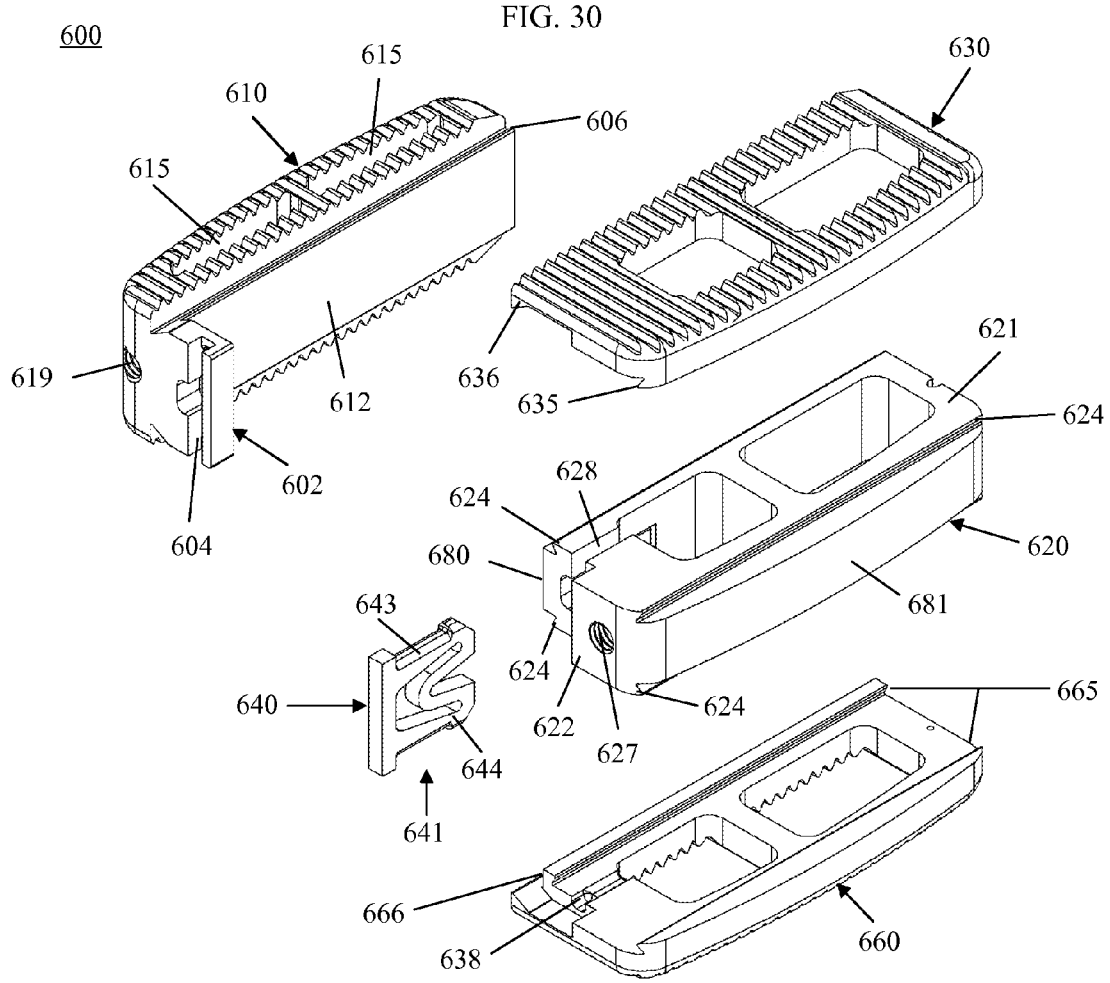
FIG. 31 is an exploded front, perspective view of the tissue spacer device of FIG. 30, in accordance with an aspect of the present invention.

An alternative embodiment tissue spacer implant is shown in FIGS. 30 and 31. According to aspects of the invention, the tissue spacer implant 600 is a vertical and horizontal expandable implant. The tissue spacer implant 600, in one embodiment, includes an intermediate spacer member 620 which engages a lateral member 610 and the coupled intermediate spacer member 620 and the lateral member 610 are positioned between and couple to a top member 630 and a bottom member 660. For example purposes, FIG. 30 shows the implant construct to have planar top and bottom surfaces, although these surfaces for some embodiments may be angled as described above with reference to implants 100, 200. If the bone contacting surfaces 634, 664 of the implant 600 are angled, the implant 600 may be used to correct deformities in vivo.

Figure 32:
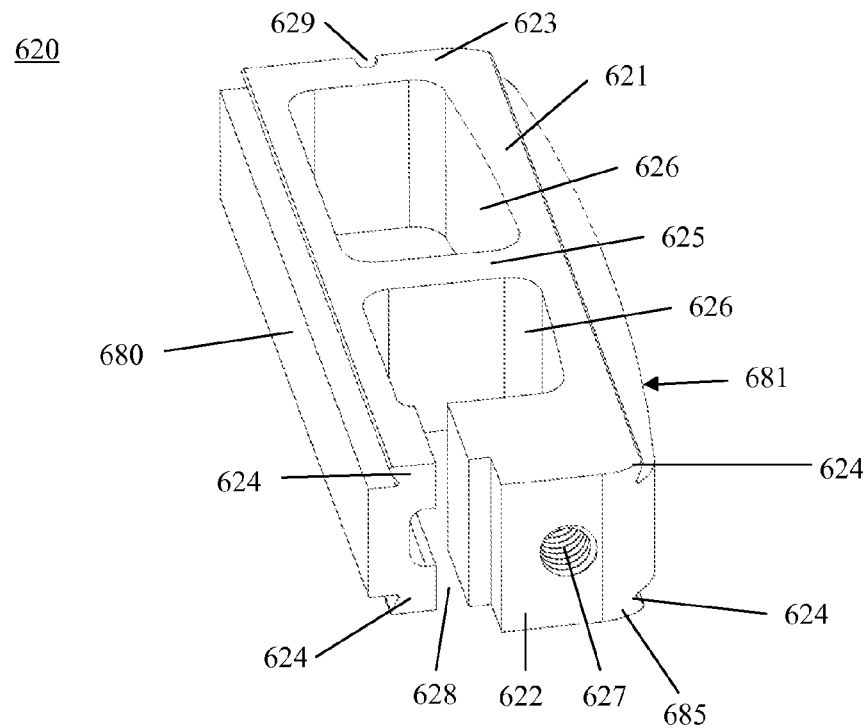
FIG. 32 is a front, perspective view of the intermediate spacer member for the tissue spacer device of FIG. 30, in accordance with an aspect of the present invention.

As shown in FIG. 32, the intermediate spacer member 620 includes a top side 621 and a bottom side 685 opposite the top side 621, as well as a first lateral side 680 and a second lateral side 681 opposite the first lateral side 680. The intermediate spacer member 620 typically includes at least two pairs of dovetails 624 disposed on the top side 621 and the bottom side 685 adapted to couple the bottom surface 632 of the top member 630, the top surface 661 of the bottom member 660, respectively, and the inner side 613 of the lateral member 610 with the intermediate spacer member 620. The top member 630, bottom member 660, and lateral member 610 may be modular and allow the surgeon to mix and match various shaped, sized, and configured members 610, 630, and 660 chosen from a kit with the intermediate spacer member 620. The kit may include a plurality of differently sized and shaped members 610, 620, 630, 660 so that the surgeon can select the desired components at the time of surgery. The intermediate spacer member 620 may also include two openings 626 that extend through the center and are separated by a central wall 625. The openings 626 are configured for packing bone grafting material into and through the entire implant 600. The intermediate spacer member 620 also has a front wall 622 and a rear wall 623. The front wall 622 may include a cutout 686 with a passageway 628 extending into the opening 626. The intermediate spacer member 620 also includes a threaded hole 627 located in the front wall 622 and offset to one side and the passageway 628 is offset to the side opposite the hole 627. The passageway 628 is configured to receive the tip or extension 642 of the locking mechanism 640, as shown in FIG. 30. The hole 627 is configured to engage an insertion device (not shown) for inserting the intermediate spacer member 620 between the members 610, 630, 660. The spacer member 620 also includes a rear wall 623 opposite the front wall 622 and the rear wall 623 may include a notch 629. The openings 626 are positioned between the front and rear walls 622, 623 and the lateral sides 680, 681 which define the length of the implant 600. The intermediate spacer member 620 may also include longitudinal female dovetails 624 positioned on the outer sides of the lateral sides 680, 681, as shown in FIG. 32. The two sets of dovetails 624 that are located on the outer surfaces of the two opposing lateral sides 680, 681 are generally parallel to each other prior to insertion of a locking mechanism 640.

Figure 33:
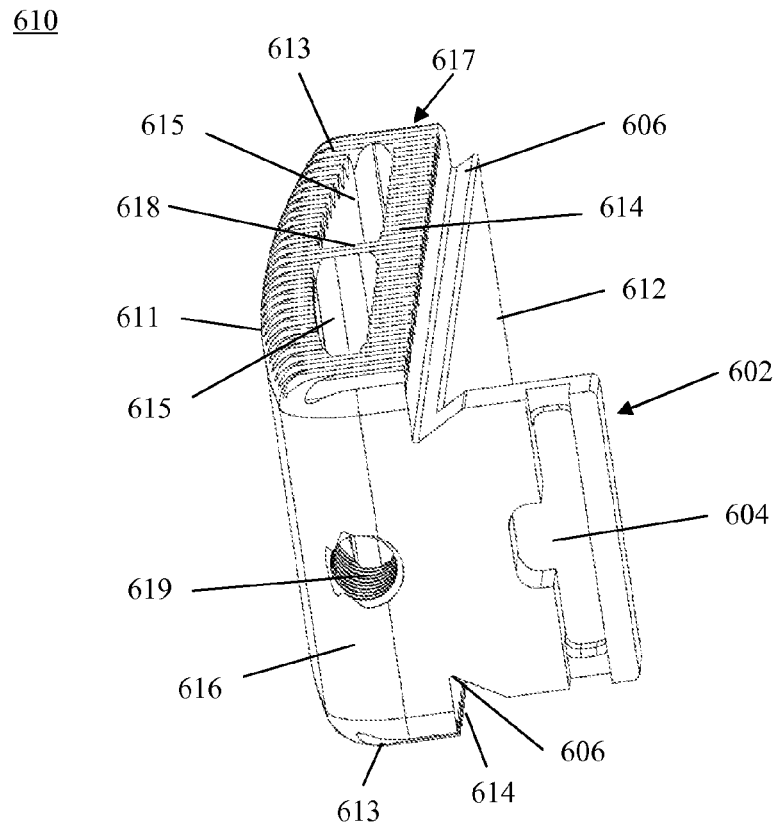
FIG. 33 is a front, perspective view of a lateral member of the tissue spacer device of FIG. 30, in accordance with an aspect of the present invention.

As shown in FIG. 33, the lateral member 610 includes an outer (lateral directed) side 611 and an inner (medial directed) side 612 opposite the outer side 611. The lateral member 610 also includes top and bottom sides 613 with bone contacting surfaces 614 disposed on each of the top and bottom sides 613. Each bone contacting surface 614 being configured to engage tissue, for example, bone, such as, vertebrae, as discussed above in greater detail with respect to the bone contacting surfaces 135 of implant 100 and which for brevity sake will not be discussed again here. The lateral member 610 may also include a central cavity 615 that is defined by the outer side 611, inner side 612, a front side 616 and a rear side 617. The cavity 615 may be divided by one or more walls 618 to create multiple cavities 615, for example, as shown in FIG. 33, there are two cavities 615. The cavities 615 are configured to enable the packing of bone graft material within the cavities 615.

Also shown in FIG. 33, the front side 616 of the lateral member 610 also includes a threaded hole 619 and an engagement member 602. The threaded hole 619 may be used for insertion of the lateral member 610 into the patient. The engagement member 602 may be configured to mate with the cutout portion 686 of the front wall 622 of the spacer member 620 and may include an opening 604 which aligns with the passageway 628 for insertion of a locking mechanism 640. The inner side 612 of the lateral member 610 also includes a pair of female dovetails 606 that are configured to slide onto engage the dovetails 636, 666 of the top and bottom members 630, 660, respectively.

Figure 34:
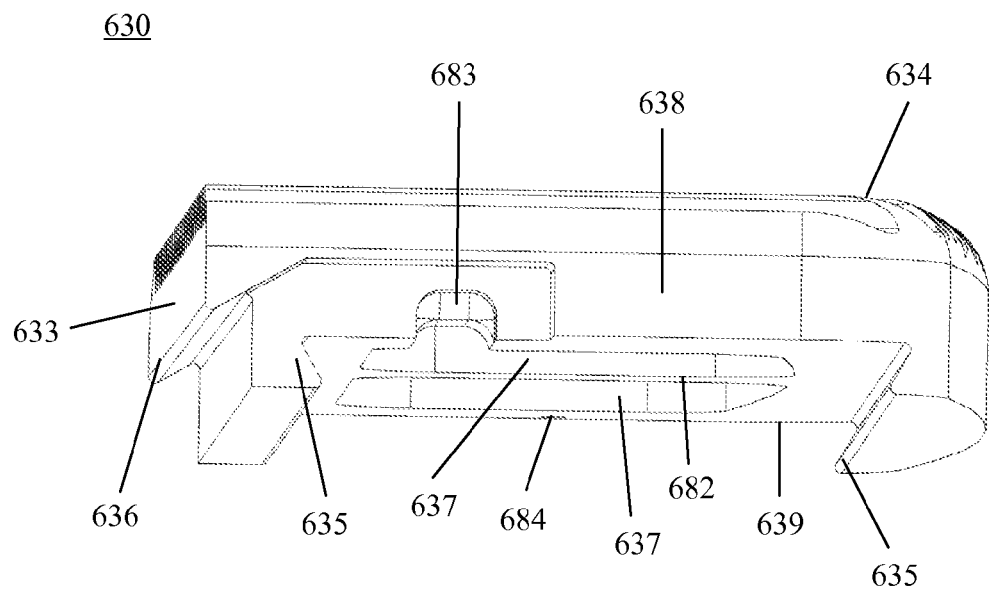
FIG. 34 is a front, perspective view of one embodiment of a top member of the tissue spacer device of FIG. 30, in accordance with an aspect of the present invention.
Figure 35:
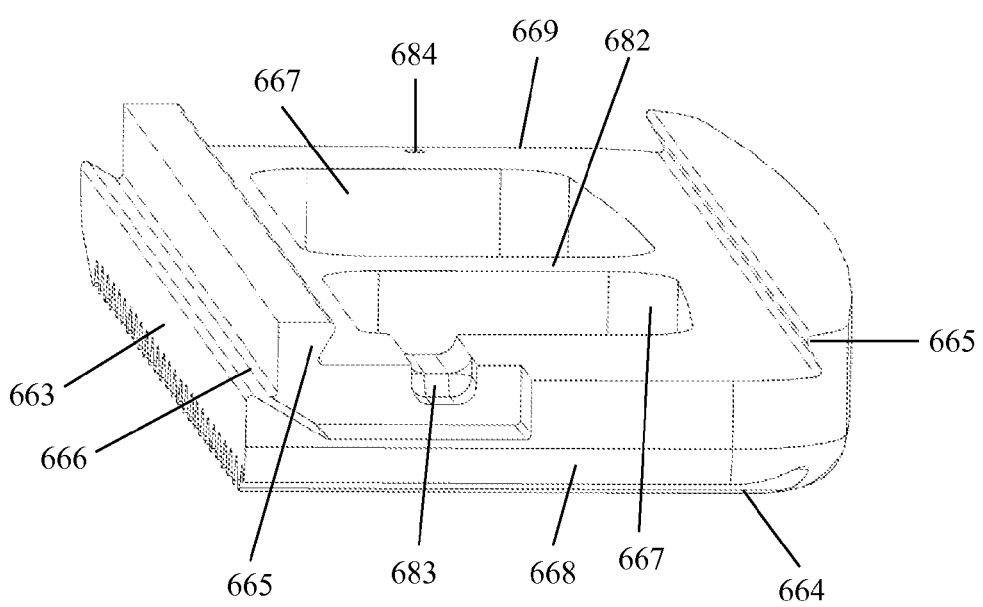
FIG. 35 is a front, perspective view of one embodiment of a bottom member of the tissue spacer device of FIG. 30, in accordance with an aspect of the present invention.

As seen in FIGS. 34 and 35, the top member 630 and bottom member 660 are mirror images of each other and have the same structural elements. The top member 630 is movingly attached to the top side 621 of the spacer member 620 and the bottom member 660 is movingly attached to the bottom side 685 of the spacer member 620. The top and bottom members 630, 660 include bone contacting surfaces 634, 664, which are generally parallel to each other and are either angled or straight. The bone contacting surfaces 634, 664 are of the type described above with reference to bone contacting surfaces 234, 264 and for brevity sake will not be described again here. In addition, the top and bottom members 630, 660 also include a notch 683 on the front wall 638, 668 configured to engage the locking mechanism when inserted into the implant 600. The top and bottom members 630, 660 may also include an opening 684 near the back wall 639, 669 for receiving one or more projections (not shown). The projections may be designed to engage the notch 629 of the spacer member 620 to securely position the spacer member 620 relative to the top and bottom members 630, 660 prior to insertion of the locking mechanism 640. The projections may also assist in preventing the spacer member 620 from sliding out the rear end of the top and bottom members 630, 660 during insertion of the spacer member 620.

FIGS. 34 and 35 also show the top and bottom members 630, 660 which may include at least one central cavity 637, 667 that is defined by the front wall 638, 668 and the back wall 639, 669, respectively. A middle wall 682 may divide the cavity 637, 667 into two separate cavities. The cavities 637, 667 enable a surgeon to pack bone growth material through the implant 600. The top and bottom members 630, 660 also each include a pair of male dovetails or angled slots 635, 665. One skilled in the art would understand that corresponding dovetails, angled slots and other correspondingly shaped configurations may be used interchangeably to align and secure the members 610, 630, 660 together. The male dovetails 635, 665 are configured to be aligned and slid into the corresponding female dovetails 624 of the spacer member 620. The dovetails 624, 635, 665, in combination, couple the top and bottom members 630, 660 to the spacer member 620. The top and bottom members 630, 660 may also each include a third, female dovetail 636, 666 on the medial side 633, 663. The female dovetails 636, 666 are configured to align and engage with the corresponding pair female dovetails 606 of the lateral member 610. The dovetails 606, 636, 666 in combination, couple the lateral member 610 to the top and bottom members 630, 660. Thus, the dovetails 624, 635, 665, 606, 636, 666 are configured to couple the top and bottom members 630, 660 to the spacer member 620 and the lateral member 610. As described above with reference to implants 100, 200, the dovetails 624, 635, 665, 606, 636, 666 may be straight or include a draft angle and for brevity sake will not be described again here.

Figure 36:
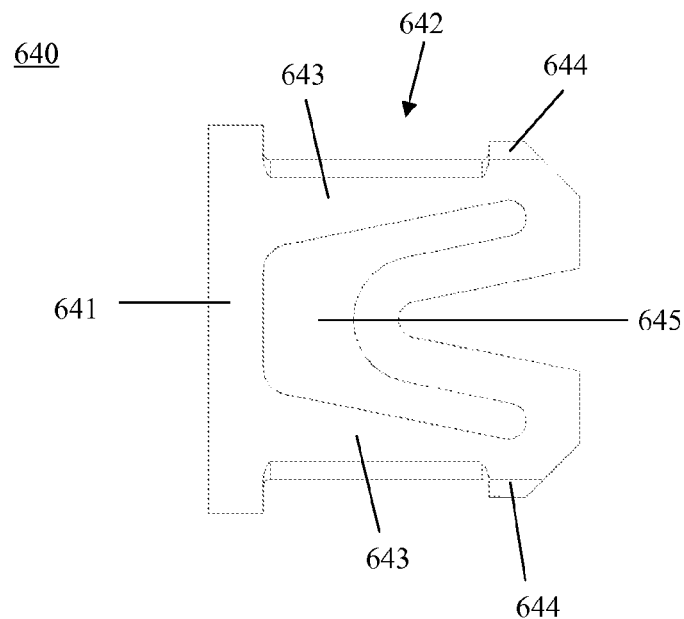
FIG. 36 is a side view of a locking mechanism for the tissue spacer device of FIG. 30, in accordance with an aspect of the present invention.
Figure 37:
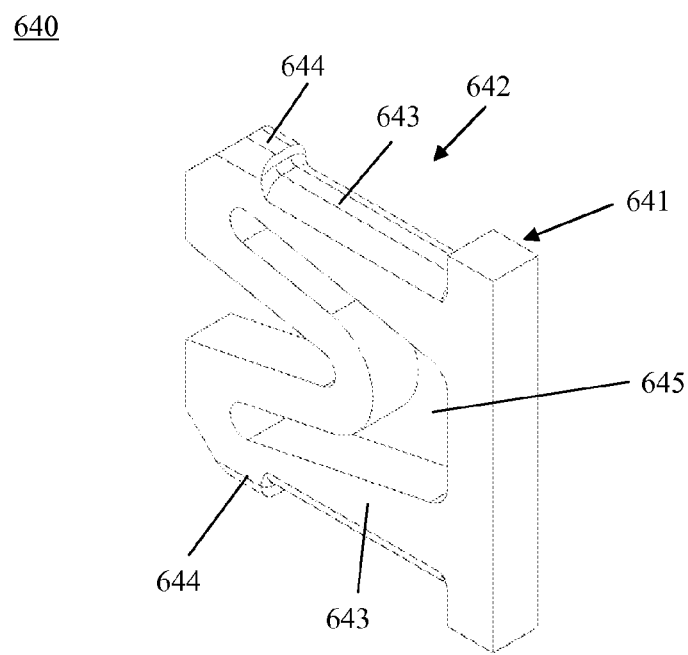
FIG. 37 is a front, perspective view of a locking mechanism for the tissue spacer device of FIG. 30, in accordance with an aspect of the present invention.

Once the four components 610, 620, 630, and 660 are coupled by the dovetails 624, 635, 665, 606, 636, 666, a locking mechanism 640 may be inserted through the opening 604 and the passageway 628 to engage the lateral member, intermediate spacer, top and bottom members 610, 620, 630, 660. As shown in FIGS. 36 and 37, the locking mechanism 640 includes a head portion 641 and an extension portion 642. The head portion 641 may engage a portion of the engagement member 602 as well as the notches 683 in the top and bottom members 630, 660. The extension portion 642 may include at least one leg 643, a protrusion 644 on each leg 643, and an opening 645. In the illustrated embodiment, there are, for example, two legs 643 each including a protrusion 644 for engaging the top and bottom members 630, 660. The legs 643 of the locking mechanism 640 are depressed in order to be inserted through opening 604 and passageway 628. After the locking mechanism 640 passes through the opening 604 in the lateral member 610, the legs 643 may expand or spring out to engage the walls of the central cavities 637, 667 of the top and bottom members 630, 660. The opening 645 may be used to remove the locking mechanism 640 from the implant 600. The locking mechanism 640 may be made of a deformable or elastic material to enable deformation for insertion and removal. A tool 700, as shown in FIG. 38, may be used to remove the locking mechanism 640 by engaging the opening 645.

Figure 38:
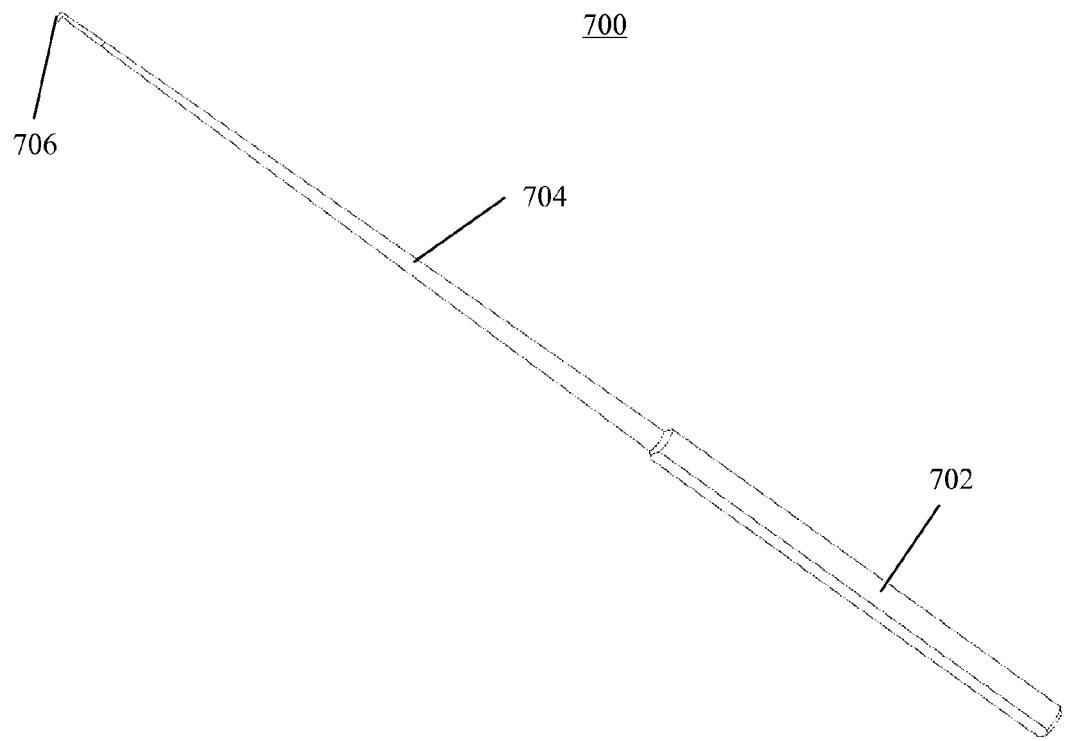
FIG. 38 is a perspective view of disassembly tool for the tissue spacer devices of FIGS. 18 and 30, in accordance with an aspect of the present invention.

As shown in FIG. 38, the tool 700 may include a handle 702 with a shaft 704 extending out from the handle 702. The shaft 704 may include a hook 706 on the end opposite the handle 702. The hook 706 may be configured to engage the opening 645 in the locking mechanism 640 to remove the locking mechanism 640 from the implant 600.

Further, it is contemplated that angled bone contacting surfaces, caps, or plates may be attached to the lateral member 610, the top member 630, and the bottom member 660 to address various skeletal deformities that are encountered clinically. It is also understood that the bone contacting surfaces of such modular surfaces, caps, or plates may include various bioactive or bone ingrowth coatings or have a range of surface topography configurations. In addition, the inner surfaces of the lateral member 610, top member 630, and bottom member 660 and the outer surfaces of the spacer member 620 may be flat to ensure easy assembly with the mating dovetails and maximum load transfer between the four joined components.

The implant 600 may be inserted into a patient using multiple insertion tools. For example, a first insertion tool of the type described above with reference to tool 500 may couple to the top and bottom members 630, 660 for implantation. In addition, a second insertion tool may couple to the lateral member 610 and be configured to travel along first and second housings, similar to the first and second housings 534, 540 of the tool 500. A third tool, for example, a tool similar to tool 400 with an alignment head configured to mate with the intermediate spacer member 620, may then be coupled to the intermediate spacer member 620 for insertion between the lateral member 610 and the top and bottom members 630, 660.

Figure 39:
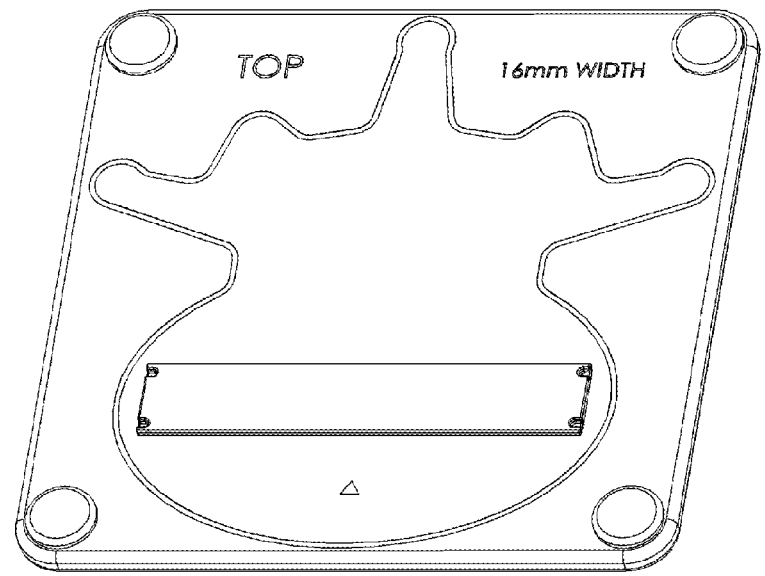
FIG. 39 is a perspective view of a bone block, in accordance with an aspect of the present invention.
Figure 40:
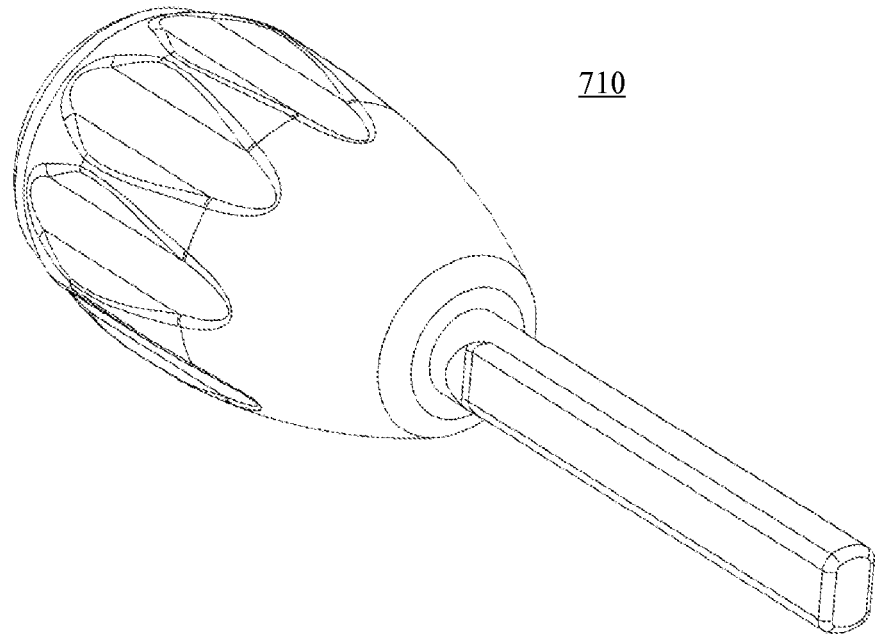
FIG. 40 is a perspective view of a bone tamp, in accordance with an aspect of the present invention.
Figure 41:
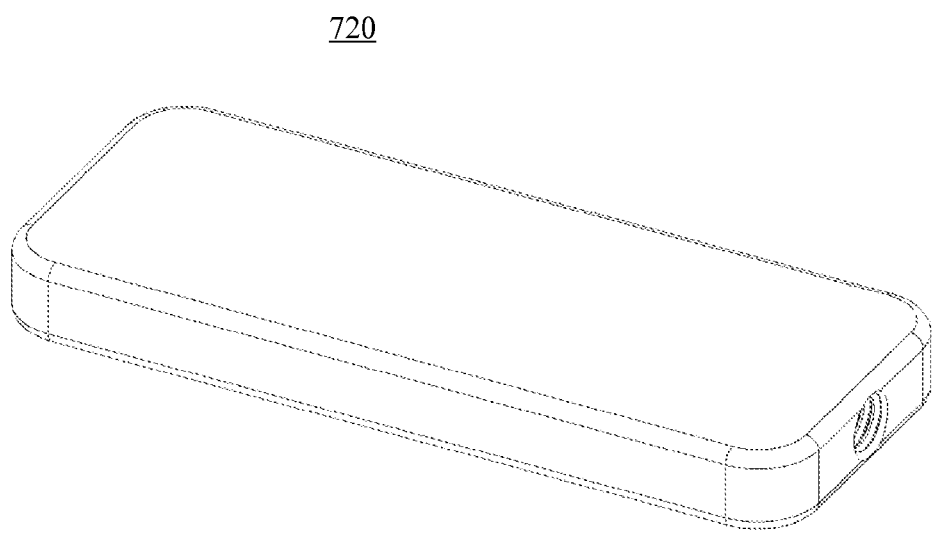
FIG. 41 is a perspective view of a foot print trial, in accordance with an aspect of the present invention.
Figure 42:
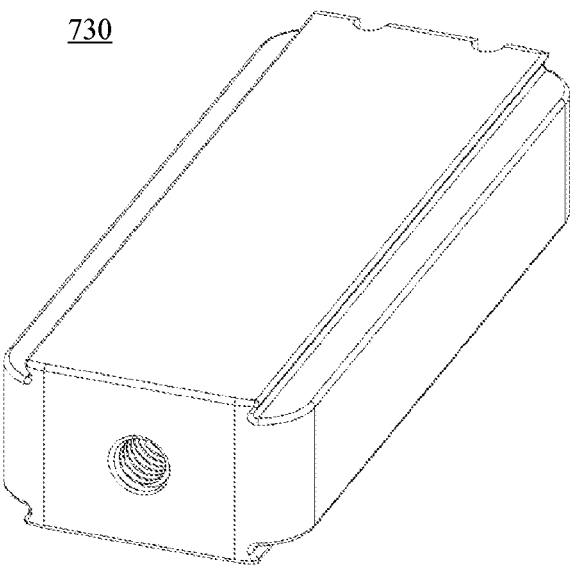
FIG. 42 is a perspective view of a spacer trial, in accordance with an aspect of the present invention.
Figure 43:
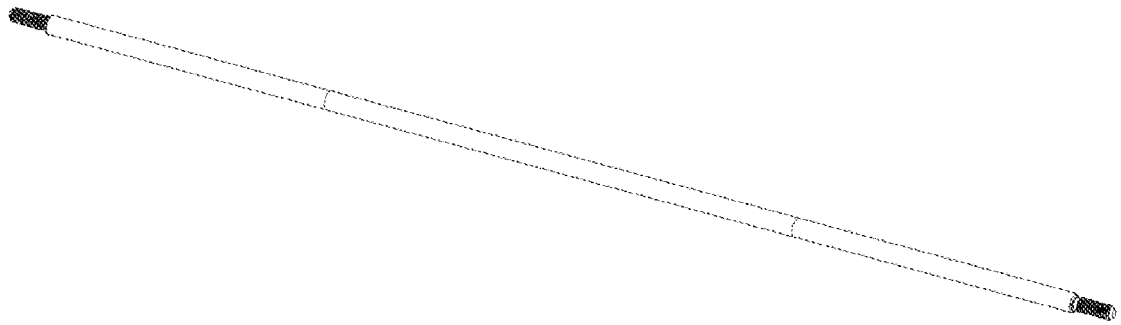
FIG. 43 is a perspective view of a trial handle, in accordance with an aspect of the present invention.

Additional figures of various sizing instruments have also been attached hereto. FIG. 39 shows a bone block 700 that is used for implant component selection and verification. FIG. 40 shows a bone tamp 710 that may be used to pack bone grafting material within the implants 100, 200, 600. A foot print trial 720 as seen in FIG. 41 may be used for in situ sizing purposes. FIG. 42 shows a spacer trial 730 that may used to ensure that the proper gap is achieve in situ or to determine what sized intermediate spacer block should be used to assemble the implants 100, 200, 600. A trial handle 740 that connects to the foot print trial 720 or other implant trials is seen in FIG. 43.

As shown in FIG. 60, the example surgical method for using the tissue spacer implants 100, 200, 600 is well known in the art, including the appropriate surgical exposure and dissection techniques. The method includes, obtaining the properly sized and configured medical device 800, for example, lateral members 130, 131, top and bottom members 230, 260 or 630, 660 and attaching these elements to a distraction/insertion tool 810, for example, tools 300, 500. Following the attachment of the lateral members 130, 131, top and bottom members 230, 260, or 630, 660 to the distraction tool, the lateral members 130, 131, top and bottom members 230, 260 or 630, 660 are placed between two tissue bodies 820. For example purposes only, we shall describe herein the technique as used in maintaining the space between two vertebral bodies. The ends of the distraction tool with the coupled and aligned lateral members 130, 131, top and bottom members 230, 260 or 630, 660 are positioned within a space within a spinal column with the lateral members 130, 131, top and bottom members 230, 260 or 630, 660 engaging the respective adjacent vertebral bodies. Upon completion of the distraction, spacing, or maintenance of the existing space with the instrument 300, 500 and calculation of the necessary thickness or width of the intermediate spacer member 120, 220, 620 the appropriate sized intermediate spacer member 120, 220, 620 is attached to an insertion tool, for example, tool 400. The intermediate spacer member 120, 220, 620 is slidingly engaged with the distraction instrument and the spacer member 120, 220, 620 is oriented and tracked into the space between at least a first and second member 830, for example, the two lateral members 130, 131, top and bottom members 230, 260 or 630, 660 allowing the pairs of dovetails 124, 224, 624 for the intermediate spacer member 120, 220, 620 to mate with the dovetails for the corresponding lateral members 130, 131, top and bottom members 230, 260, or top and bottom members 630, 660. Thus, finalizing the assembly of the implant 100, 200 into a single construct. For the implant 600, the properly sized and configured lateral member 610 is attached to an insertion tool, for example, a tool similar to tool 400 and slidingly engaged with the distraction instrument and the lateral member 610 is oriented and tracked into the space beside the top and bottom members 630, 660. Thus, finalizing the assembly of the implant 600 into a single construct.

The method may further include actuating the coupling mechanism 150 by inserting the threaded rod 140 into the hole 127 of the intermediate spacer members 120 causing the spacer insert 110 to translate and securing the intermediate spacer member 120 to the two lateral members 130, 131 via the coupling mechanism 150, thus fixing the implant 100 between two vertebral bodies within a patient's spinal column 840. Alternatively, the method may further include actuating the coupling mechanism 250, 650 by inserting the locking mechanism 240, 640 into the opening 213, 613 of the intermediate spacer members 220, 620 causing the locking mechanism 240, 640 to engage the top and bottom members 230, 260 and the coupling mechanisms 150, 250 to couple the dovetails together, thus fixing the implant 200, 600 between two vertebral bodies within a patient's spinal column 840.

The method may further include detaching the distraction/insertion instrument from the two lateral members 130, top and bottom members 230, 260 or 630, 660 and removing the instrument from inside the living body. Instruments may be removed from intermediate spacer members 120, 220, 620 and lateral member 610 and removed from inside the living body.

It should be understood by those skilled in the art that the surgical method described herein may also include alternatively, using a modular footplate that has been coupled to an alternative embodiment of the lateral members 130, 131, the top and bottom members 230, 260, or lateral, top and bottom members 610, 630, 660 to accommodate various clinical deformities or bone growth coatings.

Figure 44:
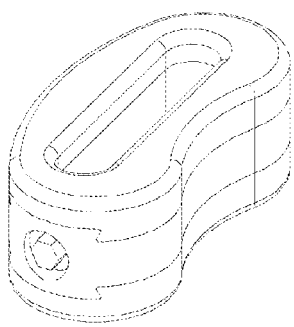
FIG. 44 is a perspective view of an alternative shaped (TLIF) vertical expandable tissue spacer, in accordance with an aspect of the present invention.
Figure 45:
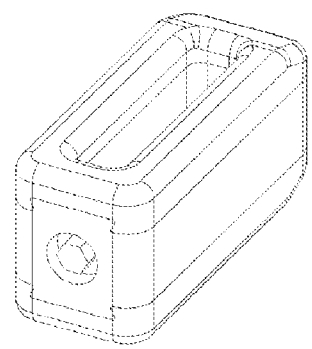
FIG. 45 is a perspective view of an alternative shaped (PLIF) vertical expandable tissue spacer, in accordance with an aspect of the present invention.
Figure 46:
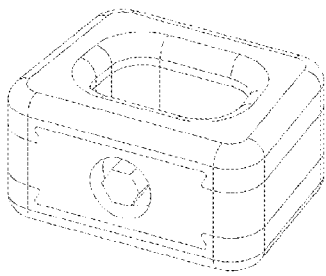
FIG. 46 is a perspective view of an alternative shaped (cervical) vertical expandable tissue spacer, in accordance with an aspect of the present invention.
Figure 47:
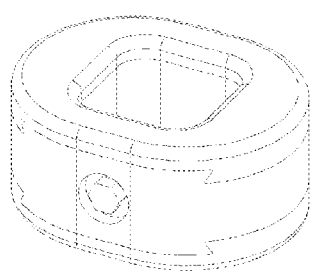
FIG. 47 is a perspective view of an alternative shaped (ALIF) vertical expandable tissue spacer, in accordance with an aspect of the present invention.
Figure 48:
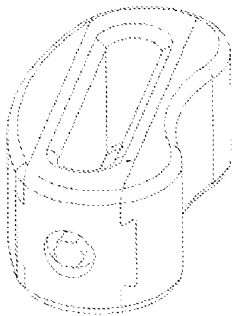
FIG. 48 is a perspective view of an alternative shaped (TLIF) horizontal expandable tissue spacer, in accordance with an aspect of the present invention.
Figure 49:
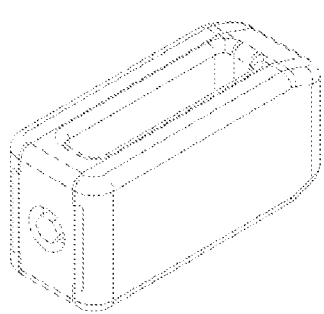
FIG. 49 is a perspective view of an alternative shaped (PLIF) horizontal expandable tissue spacer, in accordance with an aspect of the present invention.
Figure 50:
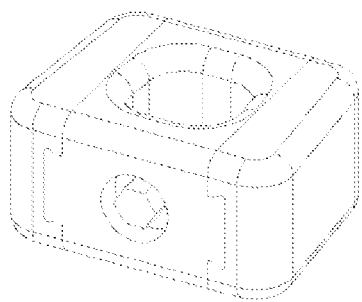
FIG. 50 is a perspective view of an alternative shaped (cervical) horizontal expandable tissue spacer, in accordance with an aspect of the present invention.
Figure 51:
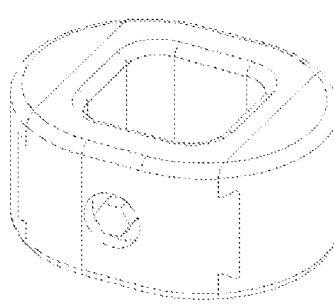
FIG. 51 is a perspective view of an alternative shaped (ALIF) horizontal expandable tissue spacer, in accordance with an aspect of the present invention.
Figure 52:
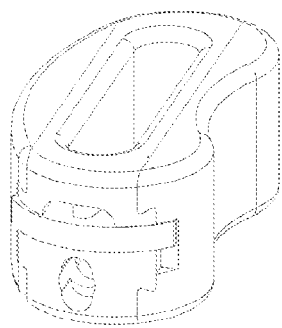
FIG. 52 is a perspective view of an alternative shaped (TLIF) horizontal expandable tissue spacer, in accordance with an aspect of the present invention.
Figure 53:
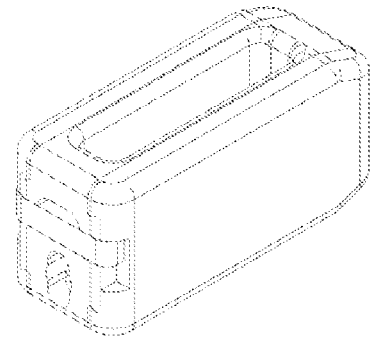
FIG. 53 is a perspective view of an alternative shaped (PLIF) horizontal expandable tissue spacer, in accordance with an aspect of the present invention.
Figure 54:
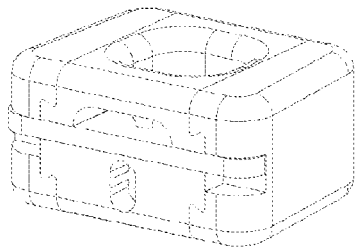
FIG. 54 is a perspective view of an alternative shaped (Cervical) horizontal expandable tissue spacer, in accordance with an aspect of the present invention.
Figure 55:
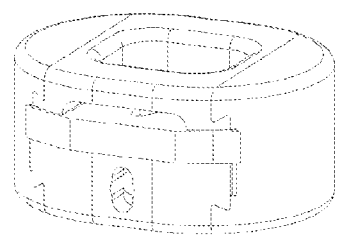
FIG. 55 is a perspective view of an alternative shaped (ALIF) horizontal expandable tissue spacer, in accordance with an aspect of the present invention.
Figure 56:
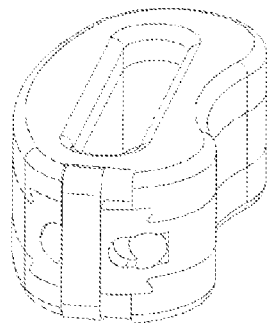
FIG. 56 is a perspective view of an alternative shaped (TLIF) vertical expandable tissue spacer, in accordance with an aspect of the present invention.
Figure 57:
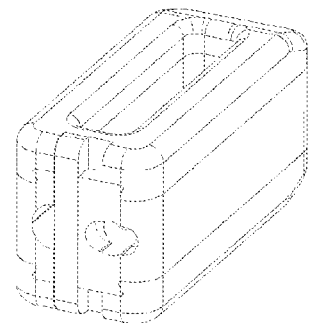
FIG. 57 is a perspective view of an alternative shaped (PLIF) vertical expandable tissue spacer, in accordance with an aspect of the present invention.
Figure 58:
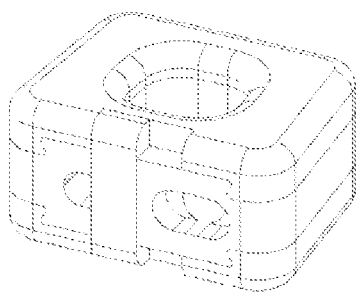
FIG. 58 is a perspective view of an alternative shaped (Cervical) vertical expandable tissue spacer, in accordance with an aspect of the present invention.
Figure 59:
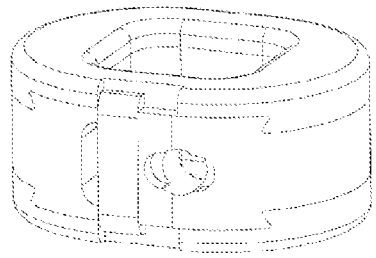
FIG. 59 is a perspective view of an alternative shaped (ALIF) vertical expandable tissue spacer, in accordance with an aspect of the present invention.

Alternative shaped embodiments of the vertical and horizontal tissue spacers are also shown in FIGS. 44-59. For example, these include a vertical transforaminal lumbar interbody fusion ("TLIF") spacer (FIG. 44), a vertical posterior lumbar interbody fusion ("PLIF") spacer (FIG. 45), a vertical cervical spacer (FIG. 46), a vertical anterior lumbar interbody fusion ("ALIF") spacer (FIG. 47), a horizontal TLIF spacer (FIG. 48), a horizontal PLIF spacer (FIG. 49), a horizontal cervical spacer (FIG. 50), and a horizontal ALIF spacer (FIG. 51), a horizontal TLIF spacer (FIG. 52), a horizontal PLIF spacer (FIG. 53), a horizontal cervical spacer (FIG. 54), and a horizontal ALIF spacer (FIG. 55), a vertical TLIF spacer (FIG. 56), a vertical PLIF spacer (FIG. 57), a vertical cervical spacer (FIG. 58), a vertical ALIF spacer (FIG. 59). The vertical and horizontal tissue spacers shown in FIGS. 44-51 may include a threaded rod or screw of the type described above with reference to threaded rod or screw 140 for implant 100. The horizontal and vertical tissue spacers shown in FIGS. 52-59 may include a locking mechanism of the type described above with reference to the locking mechanism 240 of implant 200.

As shown in FIG. 61, a method for assembling an expandable tissue spacer implant is shown. The method may include obtaining an intermediate spacer member with a coupling mechanism 900, selecting a first member with a first pair of projections 910, selecting a second member with a second pair of projections 920, engaging the first pair of projections of the first member with the coupling mechanism of the intermediate spacer member and engaging the second pair of projections of the second member with the coupling mechanism of the intermediate spacer member 930, and inserting a locking mechanism into the intermediate spacer member to actuate the coupling mechanism and secure the first member and second member to the intermediate spacer member 940.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been depicted and described with reference to example embodiments. It will be understood that the architectural and operational embodiments described herein are exemplary of a plurality of possible arrangements to provide the same general features, characteristics, and general system operation. Modifications, substitutions, and alterations will occur to others upon a reading and understanding of the preceding detailed description. It is intended that the invention be construed as including all such modifications and alterations and therefore these changes be considered to be within the scope of the following claims.

What is claimed is:

1. A vertical expandable tissue spacer implant, the implant comprising:
    a top member with a bottom surface;
    a bottom member with a top surface; and
    an intermediate spacer member having a coupling mechanism and an opening on a front wall, wherein the coupling mechanism cooperatively engages the bottom surface of the top member to the intermediate spacer member and the top surface of the bottom member to the intermediate spacer member; and
    a locking mechanism with a head portion for engaging the front wall of the intermediate spacer member and an extension portion for insertion into the opening of the intermediate spacer member and securing the top member and the bottom member to the intermediate spacer member, wherein the locking mechanism further comprises two legs each with a protrusion for engaging the top member and the bottom member.

2. The implant of claim 1, wherein the coupling mechanism, comprises:
    two pairs of extensions disposed on the intermediate spacer member;
    a pair of extensions disposed on the bottom surface of the top member; and
    a pair of extensions disposed on the top surface of the bottom member.

3. The implant of claim 2, wherein the extensions comprise dovetails.

4. The implant of claim 2, wherein the two pairs of extensions include a first pair of extensions on a top side of the intermediate spacer member and a second pair of extensions on a bottom side of the intermediate spacer member.

5. The implant of claim 4, wherein the first pair of extensions of the intermediate spacer member engage the pair of extensions on the bottom surface of the top member and the second pair of extensions of the intermediate spacer member engage the pair of extensions on the top surface of the bottom member.

6. The implant of claim 5, wherein the intermediate spacer member, the top member, and the bottom member each have a generally rectangular outside perimeter.

7. The implant of claim 1, wherein the top member further comprises at least one projection and the bottom member further comprises at least one projection, wherein the at least one projection of the top member and bottom member limits the translation of the top member and bottom member with respect to the intermediate spacer member.

8. A method of assembling an implant, comprising:
    obtaining an intermediate spacer member having a coupling mechanism;
    inserting a spacer insert into an inner cavity of the intermediate spacer member;
    selecting a first member with a first pair of projections;
    selecting a second member with a second pair of projections;
    engaging the first pair of projections of the first member to the coupling mechanism of the intermediate spacer member and engaging the second pair of projections of the second member to the coupling mechanism of the intermediate spacer member; and
    inserting a locking mechanism into the intermediate spacer member to engage the spacer insert and actuate the coupling mechanism and secure the first member and second member to the intermediate spacer member.

9. A surgical method for maintaining a space between two tissue bodies in a living being, comprising:
    obtaining a medical device comprising:
        a first member;
        a second member;
        an intermediate spacer member having a coupling mechanism and an opening on a front wall, wherein the coupling mechanism slidingly couples the first member to the intermediate spacer member and the second member to the intermediate spacer member; and
        a locking mechanism with a head portion for engaging the front wall of the intermediate spacer member and an extension portion for insertion into the opening of the intermediate spacer member and securing the top member and the bottom member to the intermediate spacer member, wherein the locking mechanism further comprises two legs each with a protrusion for engaging the top member and the bottom member;
    coupling the first and second members to an insertion instrument;
    positioning and inserting the insertion instrument with the coupled first and second members into a space between the two tissue bodies to maintain or increase the space therebetween;
    inserting the spacer insert into the inner cavity of the intermediate spacer member;

slidingly inserting the intermediate spacer member within the insertion instrument and into the space between the first and second members; and securing the intermediate spacer member to the first and second members.

10. The method of claim 9, wherein the method further comprises detaching the insertion instrument from the medical device and removing the instrument from the living being.

11. A vertical expandable tissue spacer implant, the implant comprising:

a top member with a bottom surface;

a bottom member with a top surface; and an intermediate spacer member having a coupling mechanism and an opening on a front wall, wherein the coupling mechanism cooperatively engages the bottom surface of the top member to the intermediate spacer member and the top surface of the bottom member to the intermediate spacer member;

a lateral member with a first side, wherein the coupling mechanism cooperatively engages the first side of the lateral member to the intermediate spacer member, the top member, and the bottom member; and a locking mechanism with a head portion for engaging the front wall of the intermediate spacer member and an extension portion for insertion into the opening of the intermediate spacer member and securing the top member and the bottom member to the intermediate spacer member.

12. The implant of claim 11, wherein the coupling mechanism, comprises:

two pairs of extensions disposed on the intermediate spacer member;

a pair of extensions disposed on the bottom surface of the top member; and a pair of extensions disposed on the top surface of the bottom member.

13. The implant of claim 12, wherein the two pairs of extensions include a first pair of extensions on a top side of the intermediate spacer member and a second pair of extensions on a bottom side of the intermediate spacer member.

14. The implant of claim 13, wherein the first pair of extensions of the intermediate spacer member engage the pair of extensions on the bottom surface of the top member and the second pair of extensions of the intermediate spacer member engage the pair of extensions on the top surface of the bottom member.

15. The implant of claim 14, wherein the intermediate spacer member, the top member, and the bottom member each have a generally rectangular outside perimeter.

16. The implant of claim 11, wherein the locking mechanism further comprises two legs each with a protrusion for engaging the top member and the bottom member.

17. The implant of claim 11, wherein the top member further comprises at least one projection and the bottom member further comprises at least one projection, wherein the at least one projection of the top member and bottom member limits the translation of the top member and bottom member with respect to the intermediate spacer member.

18. The implant of claim 12, wherein the extensions comprise dovetails.

* * * * *

UNITED STATES PATENT AND TRADEMARK OFFICE
CERTIFICATE OF CORRECTION

PATENT NO. : 9,693,877 B2  
APPLICATION NO. : 14/406013  
DATED : July 4, 2017  
INVENTOR(S) : Emerick et al.

Page 1 of 1

It is certified that error appears in the above-identified patent and that said Letters Patent is hereby corrected as shown below:

On the Title Page

In the Title (54): Delete "EXPANDABLE TISSUE SPACE IMPLANT AND METHOD OF USE" and insert -- EXPANDABLE TISSUE SPACER IMPLANT AND METHOD OF USE --

In the Assignee (73): Insert -- MEDIVEST, LLC, Columbia City, IN (US) --

Signed and Sealed this  
Twenty-sixth Day of September, 2017

Joseph Matal  
*Performing the Functions and Duties of the*  
*Under Secretary of Commerce for Intellectual Property and*  
*Director of the United States Patent and Trademark Office*